US010852302B2

(12) United States Patent
Naito

(10) Patent No.: US 10,852,302 B2
(45) Date of Patent: Dec. 1, 2020

(54) METHOD FOR EVALUATION OF FUNCTION OF PHAGOCYTE

(71) Applicant: MOCHIDA PHARMACEUTICAL CO., LTD., Tokyo (JP)

(72) Inventor: Katsuki Naito, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 25 days.

(21) Appl. No.: 15/258,531

(22) Filed: Sep. 7, 2016

(65) Prior Publication Data
US 2016/0377615 A1 Dec. 29, 2016

Related U.S. Application Data

(62) Division of application No. 12/994,109, filed as application No. PCT/JP2009/059453 on May 22, 2009, now Pat. No. 9,476,872.

(30) Foreign Application Priority Data

May 23, 2008 (JP) ................................ 2008-135966

(51) Int. Cl.
| G01N 33/00 | (2006.01) |
| G01N 33/569 | (2006.01) |
| C07K 14/705 | (2006.01) |
| G01N 33/50 | (2006.01) |
| C07K 16/28 | (2006.01) |

(52) U.S. Cl.
CPC . *G01N 33/56972* (2013.01); *C07K 14/70596* (2013.01); *C07K 16/2896* (2013.01); *G01N 33/5047* (2013.01); *G01N 33/5091* (2013.01); *G01N 2333/70596* (2013.01); *G01N 2800/00* (2013.01)

(58) Field of Classification Search
CPC .......................... G01N 33/56972; G01N 33/00
USPC ....................................................... 435/7.23
See application file for complete search history.

(56) References Cited

U.S. PATENT DOCUMENTS

| 7,608,684 B2 | 10/2009 | Furusako et al. |
| 2006/0068445 A1 | 3/2006 | Furusako et al. |
| 2010/0055682 A1 | 3/2010 | Schweighoffer et al. |

FOREIGN PATENT DOCUMENTS

| EP | 1 746 104 A1 | 1/2007 | |
| JP | WO2005108429 | * 11/2005 | ........... C07K 14/705 |
| WO | 02/074789 A2 | 9/2002 | |
| WO | 2005/108429 A1 | 11/2005 | |
| WO | WO2005108429 | * 11/2005 | |
| WO | 2007/132120 A2 | 11/2007 | |

OTHER PUBLICATIONS

Tilson et al. (Mastitis—Plugged Ducts and Breast Infections. From: LEAVEN, vol. 29 No. 2, Mar.-Apr. 1993, pp. 1-8).*
Sibilia et al. (Reactive arthritis or chronic infections arthritis. Ann Rheum Dis 2002 61: 580-587).*
Yaegashi et al. (Evaluation of a newly identified soluble CD14 subtype as a marker for sepsis. J. Infect Chemother (2005) 11: 234-238).*
Stubljar et al. (Diagnostic Accuracy of Presepsin (sCD14-ST) for Prediction of Bacterial Infection in Cerebrospinal Fluid Samples from Children with Suspected Bacterial Meningitis or Ventriculitis. Journal of Clinical Microbiology 2015 53(4) 1239-1244).*
Lin et al. (Soluble CD14 Levels in the Serum, Synovial Fluid, and Cerebrospinal Fluid of Patients with Various Stages of Lyme Disease. The Journal of Infectious Diseases 2000;181:1185-8).*
Danikas et al. (Prognostic value of phagocytic activity of neutrophils and monocytes in sepsis. Correlation to CD64 and CD14 antigen expression. Clinical and Experimental Immunology, 2008, 154: 87-97 87).*
Underhill et al. (Macrophage recognition of zymosan particles. Journal of Endotoxin Research, vol. 9, No. 3, 2003).*
abcam (Sandwich Elisa, 2007, pp. 1-3).*
Etzioni et al (Isr J Med Sci, 1991, 27(7): Abstract).*
Etzioni et al (Nature Reviews, 2003, 3: internet pp. 1-10).*
Mercer (Immunol Ser, 1990, 53: 39-54).*
Ayaslioglu et al., "Significant Elevation of Serum Soluble CD14 Levils in Patients with Brucellosis", Jpn. J. Infect. Dis., vol. 58, pp. 11-14, 2005, XP-002634519.
Bannerman et al., "Increased Levels of LPS-Binding Protein in Bovine Blood and Milk Following Bacterial Lipopolysaccharide Challenge." Journal of Dairy Science. vol. 86, No. 10, p. 3128-3137, 2003.
Cauwels et al., "The Origin and Function of Soluble CD14 in Experimental Bacterial Meningitis." Journal of Immunology. vol. 162, No. 8, p. 4762-4772, 1999.
Endo et al., "Atarashii Haikessho no Shindan . . ." Japan Journal of Critical Care for Endotoxemia. vol. 9, No. 1, p. 46 to 50, 2005.
Extended European Search Report, dated Jun. 1, 2011, for European Application No. 09750665.3.
Grunwald et al., "Monocytes Can Phagocytose Gram-Negative Bacteria by a CD14-Dependent Mechanism", The Journal of Immunology, vol. 157, pp. 4119-4125, 1996, XP-002634520.
Hallwirth et al., "Monocyte phagocytosis as a reliable parameter for predicting early-onset sepsis in very low birthweight infants", Early Human Development, vol. 67, pp. 1-9, 2002, XP009147681.

(Continued)

*Primary Examiner* — Sean E Aeder
(74) *Attorney, Agent, or Firm* — Birch, Stewart, Kolasch & Birch, LLP

(57) ABSTRACT

A novel convenient method for evaluating the function of a phagocyte is provided. The method assays sCD14-ST, which is a humoral factor specifically produced in phagocytosis by the phagocyte and which is stable enough for use in an assay. Also provided is a method for detecting diseases associated with the phagocytosis by the phagocyte.

4 Claims, 9 Drawing Sheets

Specification includes a Sequence Listing.

(56) References Cited

OTHER PUBLICATIONS

International Preliminary Report on Patentability and Written Opinion (PCT/IB/338, PCT/ISA/373 and PCT/ISA/237) from International Application No. PCT/JP2009/059453 dated Jan. 20, 2011.
Ishii et al., "Relationship between the phagocytotic neutrophils and the blood lactoferrin", Database Accession No. 142:408689, Igaku Kensa, vol. 54, No. 3, 2005.
Lee et al., "Elevated Milk Soluble CD14 in Bovine Mammary Glands Challenged with *Escherichia Coli* Lipopolysaccharide." Journal of Dairy Science, vol. 86, No. 7, p. 2382-2389, 2003.
Nakamura et al., "Early elevation of plasma soluble CD14 subtype, a novel biomarker for sepsis, in a rabbit cecal ligation and puncture model", Critical Care, vol. 12, Suppl. 2, P194, Poster presentation, Mar. 13, 2008, XP-002634521.
Paziak-Domańska et al., "The Lack of Relationship between Serum Content of MBL, sCD14, Anti-PPD and Anti-Hsp65 IgG and Ingestion of *Mycobacterium bovis* BCG Bacilli by Phagocytes", Archivum Immunologiae et Therapiae Experimentalis, vol. 50, pp. 337-344, 2002, XP009147684.
Shirakawa et al., "The new sepsis marker, sCD14-ST, induction mechanism in the rabbit sepsis models", Critical Care, vol. 14, Suppl. 2, P19, Poster presentation, Sep. 1, 2010, XP-002634522.
Tang et al., "Increased Activation-Induced Cell Death in Peripheral Lymphocytes of Rheumatoid Arthiritis Patients: The Mechanism of Action." Immunology. vol. 112, No. 3, p. 496-505, 2004.
Venezie et al., "Macrophage Recruitment in Different Models of Nerve Injury: Lysozyme as a Marker for Active Phagocytosis", Journal of Neuroscience Research, vol. 40, pp. 99-107, 1995, XP-002634516.
Yaegashi et al., "Evaluation of a newly identified soluble CD14 subtype as a marker for sepsis", J. Infect. Chemother., vol. 11, pp. 234-238, 2005, XP019374906.
Hiki et al. "Release of Endotoxin-binding proteins during Major Elextive Surgery; Role of Soluble CD14 in Phagocytic Actiovation", World J. Surg., vol. 24 (2000) pp. 499-506.
International Search Report from International Application No. PCT/JP2009/059453 dated Aug. 4, 2009.
Yaegashi et al., (Soluble CD14, a new sepsis diagnostic marker, 8th International Endotoxin Society Conference, Kyoto, Japan (2004) Abstract 214, p. 373.
Yaegashi et al., Soluble CD14, a new sepsis disgnostic marker; Abstracts of poster presentations 47 to 232; Nov. 15-18.

* cited by examiner

```
SEQUENCE LISTING

<160> NUMBER OF SEQ ID NOS: 6

<210> SEQ ID NO 1
<211> LENGTH: 356
<212> TYPE: PRT
<213> ORGANISM: Homo sapiens

<400> SEQUENCE: 1

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
        50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
                100                 105                 110

Met Pro Pro Leu Pro Leu Glu Ala Thr Gly Leu Ala Leu Ser Ser Leu
            115                 120                 125

Arg Leu Arg Asn Val Ser Trp Ala Thr Gly Arg Ser Trp Leu Ala Glu
        130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190
```

Leu Met Ala Ala Leu Cys Pro His Lys Phe Pro Ala Ile Gln Asn Leu
        195                 200                 205

Ala Leu Arg Asn Thr Gly Met Glu Thr Pro Thr Gly Val Cys Ala Ala
        210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
        245                 250                 255

Ser Ala Leu Asn Ser Leu Asn Leu Ser Phe Ala Gly Leu Glu Gln Val
        260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
        290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                    325                 330                 335

Thr Leu Ser Val Gly Val Ser Gly Thr Leu Val Leu Gln Gly Ala
        340                 345                 350

Arg Gly Phe Ala
        355

<210> SEQ ID NO 2
<211> LENGTH: 355
<212> TYPE: PRT
<213> ORGANISM: Oryctolagus cuniculus

<400> SEQUENCE: 2

Ser Thr Asp Thr Pro Glu Pro Cys Glu Leu Asp Asp Asp Ile Arg
1               5                   10                  15

Cys Val Cys Asn Phe Ser Asp Pro Gln Pro Asp Trp Ser Ser Ala Leu
            20                  25                  30

Gln Cys Met Pro Ala Val Gln Val Glu Met Trp Gly Gly His Ser
        35                  40                  45

Leu Glu Gln Phe Leu Arg Gln Ala Asp Leu Tyr Thr Asp Gln Arg Arg
    50                  55                  60

Tyr Ala Asp Val Val Lys Ala Leu Arg Val Arg Arg Leu Thr Val Gly
65                  70                  75                  80

Ala Val Gln Val Pro Ala Pro Leu Leu Leu Gly Val Leu Arg Val Leu
                85                  90                  95

Gly Tyr Ser Arg Leu Lys Glu Leu Ala Leu Glu Asp Ile Glu Val Thr
            100                 105                 110

Gly Thr Ala Pro Pro Pro Pro Leu Glu Ala Thr Gly Pro Ala Leu
        115                 120                 125

Ser Thr Leu Ser Leu Arg Asn Val Ser Trp Pro Lys Gly Gly Ala Trp
    130                 135                 140

Leu Ser Glu Leu Gln Gln Trp Leu Lys Pro Gly Leu Gln Val Leu Asn
145                 150                 155                 160

Ile Ala Gln Ala His Thr Leu Ala Phe Ser Cys Glu Gln Val Arg Thr
                165                 170                 175

Phe Ser Ala Leu Thr Thr Leu Asp Leu Ser Glu Asn Pro Gly Leu Gly
            180                 185                 190

Glu Arg Gly Leu Val Ala Ala Leu Cys Pro His Lys Phe Pro Ala Leu

```
            195                 200                 205
Gln Asp Leu Ala Leu Arg Asn Ala Gly Met Lys Thr Leu Gln Gly Val
    210                 215                 220

Cys Ala Ala Leu Ala Glu Ala Gly Val Gln Pro His His Leu Asp Leu
225                 230                 235                 240

Ser His Asn Ser Leu Arg Ala Asp Thr Gln Arg Cys Ile Trp Pro Ser
                245                 250                 255

Ala Leu Asn Ser Leu Asn Leu Ser Phe Thr Gly Leu Gln Gln Val Pro
            260                 265                 270

Lys Gly Leu Pro Ala Lys Leu Asn Val Leu Asp Leu Ser Cys Asn Lys
        275                 280                 285

Leu Asn Arg Ala Pro Gln Pro Gly Glu Leu Pro Lys Val Val Asn Leu
    290                 295                 300

Ser Leu Asp Gly Asn Pro Phe Leu Val Pro Gly Ala Ser Lys Leu Gln
305                 310                 315                 320

Glu Asp Leu Thr Asn Ser Gly Val Phe Pro Ala Cys Pro Ser Pro Ser
                325                 330                 335

Leu Ala Met Gly Met Ser Gly Thr Leu Ala Leu Leu Gln Gly Ala Arg
            340                 345                 350

Gly Phe Ile
        355

<210> SEQ ID NO 3
<211> LENGTH: 351
<212> TYPE: PRT
<213> ORGANISM: Mus musculus

<400> SEQUENCE: 3

Ser Pro Ala Pro Pro Glu Pro Cys Glu Leu Asp Glu Glu Ser Cys Ser
1               5                   10                  15

Cys Asn Phe Ser Asp Pro Lys Pro Asp Trp Ser Ser Ala Phe Asn Cys
                20                  25                  30

Leu Gly Ala Ala Asp Val Glu Leu Tyr Gly Gly Gly Arg Ser Leu Glu
            35                  40                  45

Tyr Leu Leu Lys Arg Val Asp Thr Glu Ala Asp Leu Gly Gln Phe Thr
    50                  55                  60

Asp Ile Ile Lys Ser Leu Ser Leu Lys Arg Leu Thr Val Arg Ala Ala
65                  70                  75                  80

Arg Ile Pro Ser Arg Ile Leu Phe Gly Ala Leu Arg Val Leu Gly Ile
                85                  90                  95

Ser Gly Leu Gln Glu Leu Thr Leu Glu Asn Leu Glu Val Thr Gly Thr
            100                 105                 110

Ala Pro Pro Pro Leu Leu Glu Ala Thr Gly Pro Asp Leu Asn Ile Leu
        115                 120                 125

Asn Leu Arg Asn Val Ser Trp Ala Thr Arg Asp Ala Trp Leu Ala Glu
    130                 135                 140

Leu Gln Gln Trp Leu Lys Pro Gly Leu Lys Val Leu Ser Ile Ala Gln
145                 150                 155                 160

Ala His Ser Leu Asn Phe Ser Cys Glu Gln Val Arg Val Phe Pro Ala
                165                 170                 175

Leu Ser Thr Leu Asp Leu Ser Asp Asn Pro Glu Leu Gly Glu Arg Gly
            180                 185                 190

Leu Ile Ser Ala Leu Cys Pro Leu Lys Phe Pro Thr Leu Gln Val Leu
        195                 200                 205
```

```
Ala Leu Arg Asn Ala Gly Met Glu Thr Pro Ser Gly Val Cys Ser Ala
    210                 215                 220

Leu Ala Ala Ala Arg Val Gln Leu Gln Gly Leu Asp Leu Ser His Asn
225                 230                 235                 240

Ser Leu Arg Asp Ala Ala Gly Ala Pro Ser Cys Asp Trp Pro Ser Gln
                245                 250                 255

Leu Asn Ser Leu Asn Leu Ser Phe Thr Gly Leu Lys Gln Val Pro Lys
            260                 265                 270

Gly Leu Pro Ala Lys Leu Ser Val Leu Asp Leu Ser Tyr Asn Arg Leu
        275                 280                 285

Asp Arg Asn Pro Ser Pro Asp Glu Leu Pro Gln Val Gly Asn Leu Ser
290                 295                 300

Leu Lys Gly Asn Pro Phe Leu Asp Ser Glu Ser His Ser Glu Lys Phe
305                 310                 315                 320

Asn Ser Gly Val Val Thr Ala Gly Ala Pro Ser Ser Gln Ala Val Ala
                325                 330                 335

Leu Ser Gly Thr Leu Ala Leu Leu Leu Gly Asp Arg Leu Phe Val
            340                 345                 350

<210> SEQ ID NO 4
<211> LENGTH: 353
<212> TYPE: PRT
<213> ORGANISM: Bos taurus

<400> SEQUENCE: 4

Asp Thr Thr Glu Pro Cys Glu Leu Asp Asp Asp Phe Arg Cys Val
1               5                   10                  15

Cys Asn Phe Thr Asp Pro Lys Pro Asp Trp Ser Ser Ala Val Gln Cys
                20                  25                  30

Met Val Ala Val Glu Val Glu Ile Ser Ala Gly Gly Arg Ser Leu Glu
            35                  40                  45

Gln Phe Leu Lys Gly Ala Asp Thr Asn Pro Lys Gln Tyr Ala Asp Thr
    50                  55                  60

Ile Lys Ala Leu Arg Val Arg Arg Leu Lys Leu Gly Ala Ala Gln Val
65                  70                  75                  80

Pro Ala Gln Leu Leu Val Ala Val Leu Arg Ala Leu Gly Tyr Ser Arg
                85                  90                  95

Leu Lys Glu Leu Thr Leu Glu Asp Leu Glu Val Thr Gly Pro Thr Pro
            100                 105                 110

Pro Thr Pro Leu Glu Ala Ala Gly Pro Ala Leu Thr Thr Leu Ser Leu
        115                 120                 125

Arg Asn Val Ser Trp Thr Thr Gly Gly Ala Trp Leu Gly Glu Leu Gln
    130                 135                 140

Gln Trp Leu Lys Pro Gly Leu Arg Val Leu Asn Ile Ala Gln Ala His
145                 150                 155                 160

Ser Leu Ala Phe Pro Cys Ala Gly Leu Ser Thr Phe Glu Ala Leu Thr
                165                 170                 175

Thr Leu Asp Leu Ser Asp Asn Pro Ser Leu Gly Asp Ser Gly Leu Met
            180                 185                 190

Ala Ala Leu Cys Pro Asn Lys Phe Pro Ala Leu Gln Tyr Leu Ala Leu
        195                 200                 205

Arg Asn Ala Gly Met Glu Thr Pro Ser Gly Val Cys Ala Ala Leu Ala
    210                 215                 220

Ala Ala Arg Val Gln Pro Gln Ser Leu Asp Leu Ser His Asn Ser Leu
225                 230                 235                 240
```

```
Arg Val Thr Ala Pro Gly Ala Thr Arg Cys Val Trp Pro Ser Ala Leu
                245                 250                 255

Arg Ser Leu Asn Leu Ser Phe Ala Gly Leu Glu Gln Val Pro Lys Gly
                260                 265                 270

Leu Pro Pro Lys Leu Ser Val Leu Asp Leu Ser Cys Asn Lys Leu Ser
            275                 280                 285

Arg Glu Pro Arg Arg Asp Glu Leu Pro Glu Val Asn Asp Leu Thr Leu
        290                 295                 300

Asp Gly Asn Pro Phe Leu Asp Pro Gly Ala Leu Gln His Gln Asn Asp
305                 310                 315                 320

Pro Met Ile Ser Gly Val Val Pro Ala Cys Ala Arg Ser Ala Leu Thr
                325                 330                 335

Met Gly Val Ser Gly Ala Leu Ala Leu Leu Gln Gly Ala Arg Gly Phe
                340                 345                 350

Ala

<210> SEQ ID NO 5
<211> LENGTH: 20
<212> TYPE: PRT
<213> ORGANISM: Artificial sequence
<220> FEATURE:
<223> OTHER INFORMATION: Sites 40-59 of Rabbit CD14

<400> SEQUENCE: 5

Val Glu Met Trp Gly Gly Gly His Ser Leu Glu Gln Phe Leu Arg Gln
1               5                   10                  15

Ala Asp Leu Tyr
            20

<210> SEQ ID NO 6
<211> LENGTH: 30
<212> TYPE: PRT
<213> ORGANISM: Artificial sequence
<220> FEATURE:
<223> OTHER INFORMATION: Sites 1-30 of Rabbit CD14

<400> SEQUENCE: 6

Ser Thr Asp Thr Pro Glu Pro Cys Glu Leu Asp Asp Asp Ile Arg
1               5                   10                  15

Cys Val Cys Asn Phe Ser Asp Pro Gln Pro Asp Trp Ser Ser
                20                  25                  30
```

METHOD FOR EVALUATION OF FUNCTION OF PHAGOCYTE

CROSS-REFERENCE TO RELATED APPLICATIONS

This application is a Divisional of co-pending application Ser. No. 12/994,109 filed on Nov. 22, 2010, which is a National Phase of PCT International Application No. PCT/JP2009/059453 filed on May 22, 2009, which claims priority under 35 U.S.C. § 119(a) to Patent Application No. 2008-135966 filed in Japan on May 23, 2008. All of the above applications are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "20101119_SequenceListing_1110_0412PUS1.txt" created on Nov. 19, 2010 and is 13,209 bytes in size. The sequence listing contained in this .txt file is part of the specification and is hereby incorporated by reference herein in its entirety.

TECHNICAL FIELD

The present invention relates to a novel method for evaluating the function of a phagocyte and a method for detecting diseases associated with phagocytosis by the phagocyte.

BACKGROUND ART

A phagocyte is a generic concept for cells having phagocytic activity. A phagocyte is broadly divided into professional phagocytes such as neutrophils, macrophages, or dendritic cells whose main function is phagocytosis in the living body, and amateur phagocytes which occasionally exhibit phagocytic activity under a certain set of conditions. Exemplary amateur phagocytes include microglia cells of brain, Kupffer cells of liver, and Sertoli cells of testis.

A leukocyte is a cell component of blood, and the leukocyte is mainly constituted from granulocytes (about 60%), lymphocytes (about 25%), and monocytes (about 5%). Granulocytes can be further divided into neutrophils, eosinophils, and basophils. The neutrophils outnumber other types of the leukocyte, and it constitute about half of the leukocyte. The monocytes migrate through various tissues to become macrophages. Since a leukocyte includes many phagocytes and they can be isolated therefrom with ease, it is a preferable source of phagocytes.

Phagocytosis is one of the most important defense mechanisms that start at the earliest timing against invasion by microorganisms such as bacteria or fungi. Phagocytosis proceeds through sequential steps of recognizing a foreign substance by a phagocyte, intaking the foreign substance, forming a phagosome, digesting the foreign substance in the phagosome, and absorption or excretion of the digested substance. Phagocytosis occurs not only for foreign substances such as bacteria or fungi, but also on autologous substances no longer needed in the body such as residue of the autologous tissue at the site of inflammation and waste autologous cell. A phagocyte does not only digest the engulfed substances in the cell, but in some cases, it releases oxygen radicals and proteases to the exterior of the cell during the phagocytosis. While this may enable efficient local disinfection and tissue digestion, the excessive phagocytosis may result in the destruction of the autologous tissue. For example, in the lesion of rheumatoid arthritis (RA), cells which have excessively engulfed the autoimmune complex (RA cell) are found, and in such lesion, the tissue is damaged by the protease released from the RA cell, and this contributes for the progress of the arthritis.

Methods known for assaying the phagocytic function of a phagocyte include the method in which the phagocyte is brought in touch with latex particles and the latex particles engulfed in the cell is counted by means of cytometry or microscopic observation, the method in which the phagocyte is allowed to engulf fluorescence-labeled substance (*E. coli*, zymosan, and the like), and the amount of the substance engulfed by the phagocyte is detected, the method in which number of viable bacteria is confirmed by cultivation after the phagocytosis of the living bacteria, and the method in which luminescence from oxygen radical during the phagocytosis is detected.

CD14 molecule is a glycoprotein which has been identified as a differentiation maker expressed on the monocyte membrane, and it is known to have the function of a receptor for LPS (lipopolysaccharide) (Non-Patent Literature 1). Known molecular species of the CD14 molecule include two types, namely, membrane-bound CD14 (mCD14) which is expressed on the cell surface and soluble CD14 (sCD14). Known sCD14 molecular species include the one having a molecular weight of about 55 kDa and the one having a molecular weight of about 49 kDa and these are believed to be produced by secretion from liver as well as cleavage by mCD14 enzyme associated by the activation of a monocyte (Non-Patent Literatures 2 to 4).

The sCD14 having a molecular weight of about 55 kDa and the one having a molecular weight of about 49 kDa (hereinafter referred to "high molecular weight sCD14") are reported to increase in the blood of patients suffering from sepsis, acquired immunodeficiency syndrome (AIDS), acute respiratory distress syndrome (ARDS), systemic lupus erythematosus (SLE), and many other diseases. Accordingly, these sCD14 are not considered to be disease-specific markers (Non-Patent Literatures 5 to 6).

In the meanwhile, sCD14-ST (soluble CD14 antigen subtype) has been reported as a new sCD14 molecular species which shows characteristic increase in the blood concentration in sepsis patients.

sCD14-ST is a sCD14 which has a molecular weight of 13±2 kDa when electrophoresed under non-reducing conditions on SDS-PAGE, and which retains N terminal region of the CD14. Compared to the high molecular weight sCD14, sCD14-ST lacks extensive region on the C terminal side of the amino acid sequence, and it does not have LPS binding ability that the high molecular weight sCD14 has. sCD14-ST also exhibits an immunogenicity different from that of the high molecular weight sCD14, and it can be differentiated from the high molecular weight sCD14 by using antibodies. Blood concentration of the sCD14-ST is specifically high in sepsis patients (Patent Literature 1). It has also been reported that the blood concentration of the sCD14-ST is high in the sepsis patients compared to patients of systemic inflammatory response syndrome (SIRS), which is a disease whose differentiation from sepsis has been difficult. Accordingly, sCD14-ST has been considered to be a specific diagnosis marker of sepsis (Non-Patent Literature 7).

CITATION LIST

Patent Literature

[Patent Literature 1] WO 2005/108429

Non-Patent Literature

[Non-Patent Literature 1] Wright et al., Science, 249: 1431-1433, 1990.
[Non-Patent Literature 2] Bazil and Strominger, Journal of Immunology, 147: 1567-1574, 1991.
[Non-Patent Literature 3] Bufler et al., European Journal of Immunology, 25: 604-610, 1995.
[Non-Patent Literature 4] Su et al., Journal of Hepatology, 31: 435-442, 1999.
[Non-Patent Literature 5] Hayashi et al., Infection and Immunity, 67: 417-420, 1999.
[Non-Patent Literature 6] Lawn et al., Clinical & Experimental Immunology, 120: 483-487, 2000.
[Non-Patent Literature 7] Yaegashi et al., Journal of Infection and Chemotherapy 11: 234-238, 2005.

SUMMARY OF INVENTION

Technical Problems

Conventional methods used for assaying a phagocytosis function of a phagocyte required time-consuming and troublesome operations such as preliminary labeling of the substance to be engulfed, cultivation for the confirmation of the living bacteria remaining after the phagocytosis, and microscopic observation, as well as specialized apparatus such as cytometer and microscope, and accordingly, development of a more convenient new assay method has been awaited. While a convenient quantitative assay method can be developed if the humoral factor released from the phagocyte during the phagocytosis could be measured, cytokine is not adequate for use as a phatocytosis-specific marker since it is produced by various types of immunostimulative stimuli other than the stimulus by the phagocytosis. Oxygen radical was also unsuitable for use as a phatocytosis-specific marker since it is produced by various stimuli, and the oxygen radical also has the drawback that it disappears in short time resulting in the limitation that the assay needs to be carried out immediately after the phagocytosis.

In the case of diseases (such as rheumatoid arthritis) related to the local phagocytosis, diagnosis of the disease would be greatly facilitated if an assay could be developed that would allow a marker molecule in the analyte such as body fluid be assayed to determine the degree of the phagocytosis, and in such a case, a convenient assay can be designed if a humoral factor in the analyte could be used for the assay. However, no phagocytosis-specific humoral factor which is stable enough for an assay has been known to the art.

Solution to Problems sCD14-ST is a disease marker which has been known to increase in the plasma of sepsis patients. However, the mechanism of its production has been unclear. Under such situation, the inventors of the present invention found that, while blood sCD14-ST does not increase in the endotoxin-induced rabbit sepsis model animal, it increases in rabbit sepsis model animal (CLP (cecal ligation and puncture) model) that has been infected with live bacteria. Based on these experimental findings, the inventors understood that activation of the leukocyte by endotoxin is not enough for the sCD14-ST production, and phagocytosis of the bacteria by the leukocyte is important. The inventors then made an intensive study on the relation between various leukocyte stimulants and amount of the sCD14-ST produced in vitro, and found that sCD14-ST is produced only after adding a substance capable of inducing the leukocyte phagocytosis, and the production of sCD14-ST decreases by the addition a substance that inhibits the phagocytosis. The inventors also found that, in the case of the rabbit arthritis model animal, sCD14-ST in synovial fluid increases with the onset of the arthritis.

As indicated by these findings, sCD14-ST is a phagocytosis-specific humoral factor that is stable enough for use in an assay.

Accordingly, the present invention provides a novel method for evaluating the function of a phagocyte.

(1-1) A method for evaluating the function of a phagocyte by assaying sCD14-ST produced by the phagocyte.

(1-2) The method according to the above (1-1) wherein the function of the phagocyte is phagocytosis.

(1-3) The method according to the above (1-1) or (1-2) wherein the method comprising a step of contacting a substance to be engulfed with the phagocyte.

(1-4) A method for evaluating the function of a phagocyte comprising the steps of
1) bringing a phagocyte in contact with a substance to be engulfed by the phagocyte,
2) measuring sCD14-ST produced by the phagocyte, and
3) comparing the measured value with a standard value to determine presence and/or degree of the phagocytosis by the phagocyte.

(1-5) The method according to any one of the above (1-1) to (1-4) wherein the phagocyte is a neutrophil, a granulocyte, and/or a leukocyte.

(1-6) The method according to any one of the above (1-1) to (1-4) wherein the phagocyte is granulocyte, and the phagocyte function is phagocytosis.

The present invention also provides a marker containing sCD14-ST for evaluating the function of a phagocyte.

The present invention also provides various detection and evaluation methods which are enabled by evaluating the function of a phagocyte from the subject.

(2-1) A method for detecting a disease associated with a phagocyte dysfunction by evaluating the function of a phagocyte, comprising the steps of
1) evaluating the function of a phagocyte collected from a subject by the method according to any one of the above (1-1) to (1-6),
2) comparing the evaluation result with a normal value, and
3) determining the presence and/or severity of the disease based on whether the function of the phagocyte from the subject is higher or lower than the normal value.

(2-2) A method for evaluating the immune function by evaluating the function of a phagocyte, comprising the steps of
1) evaluating the function of a phagocyte collected from a subject by the method according to any one of the above (1-1) to (1-6),
2) comparing the evaluation result with a normal value, and
3) determining the degree of the immune function based on whether the function of the phagocyte from the subject is higher or lower than the normal value.

(2-3) A method for evaluating the effects of a drug by evaluating the function of a phagocyte, comprising the steps of 1) evaluating the function of a phagocyte collected from a subject during and/or after the drug administration by the method according to any one of the above (1-1) to (1-6), 2) comparing the evaluation result with a normal value and/or the evaluation result before the drug administration, and 3) determining the presence and/or degree of the change in the function of the phagocyte from the subject by the drug administration.

(2-4) A method for evaluating quality of a phagocyte for transplantation, comprising the steps of 1) evaluating the function of a hagocyte for transplantation by the method according to any one of the above (1-1) to (1-6), 2) comparing the evaluation result with a standard value, and 3) determining whether the function of the phagocyte for transplantation satisfies the standard value.

(2-5) The method according to any one of the above (2-1) to (2-4) wherein the phagocyte is a neutrophil, a granulocyte, and/or a leukocyte.

(2-6) The method according to any one of the above (2-1) to (2-5) wherein the function of the phagocyte is the phagocytosis.

(2-7) The method according to any one of the above (2-1) to (2-4) wherein the phagocyte is granulocyte and the function of the phagocyte is phagocytosis.

The present invention also provides a method for screening a substance which regulates a phagocytosis function.

(3-1) A method for screening a substance which regulates a phagocytosis function comprising the steps of 1) bringing a phagocyte in contact with an analyte, 2) measuring sCD14-ST produced by the phagocyte, and 3) evaluating effect of the analyte on the phagocytosis function of the phagocyte.

(3-2) The method according to the above (3-1) wherein the phagocyte and the analyte are contacted in the presence of a substance to be engulfed phagocyte.

(3-3) The method according to any one of the above (3-1) to (3-2) wherein the phagocyte is a neutrophil, a granulocyte, and/or a leukocyte.

The present invention also provides a method for detecting a disease associated with phagocytosis by a phagocyte.

(4-1) A method for detecting disease associated with phagocytosis by a phagocyte comprising the steps of 1) measuring the amount of sCD14-ST in a specimen (which is not blood) from the donor, 2) comparing the evaluation result with a normal value, and 3) determining whether the amount of the sCD14-ST in the specimen is higher than the normal value.

(4-2) The method according to the above (4-1) wherein sCD14-ST is measured after adding the substance to be engulfed to the specimen.

(4-3) The method according to the above (4-1) or (4-2) wherein the disease associated with phagocytosis by the phagocyte is rheumatoid arthritis, and the specimen is synovial fluid.

(4-4) The method according to the above (4-1) or (4-2) wherein the disease associated with phagocytosis by the phagocyte is mastitis and the specimen is milk.

(4-5) The method according to any one of the above (4-1) to (4-4) wherein the phagocyte is a neutrophil, a granulocyte, and/or a leukocyte.

Advantageous Effects of Invention

The present invention enables specific and convenient assay of the phagocyte function by measuring the sCD14-ST which is a humoral factor released from the phagocyte during the phagocytosis. The present invention also enables screening for the phagocytic function-regulating substance by using the assay system. Furthermore, the present invention also enables specific and convenient detection of the disease associated with phagocytosis by the phagocyte.

Figure 1:
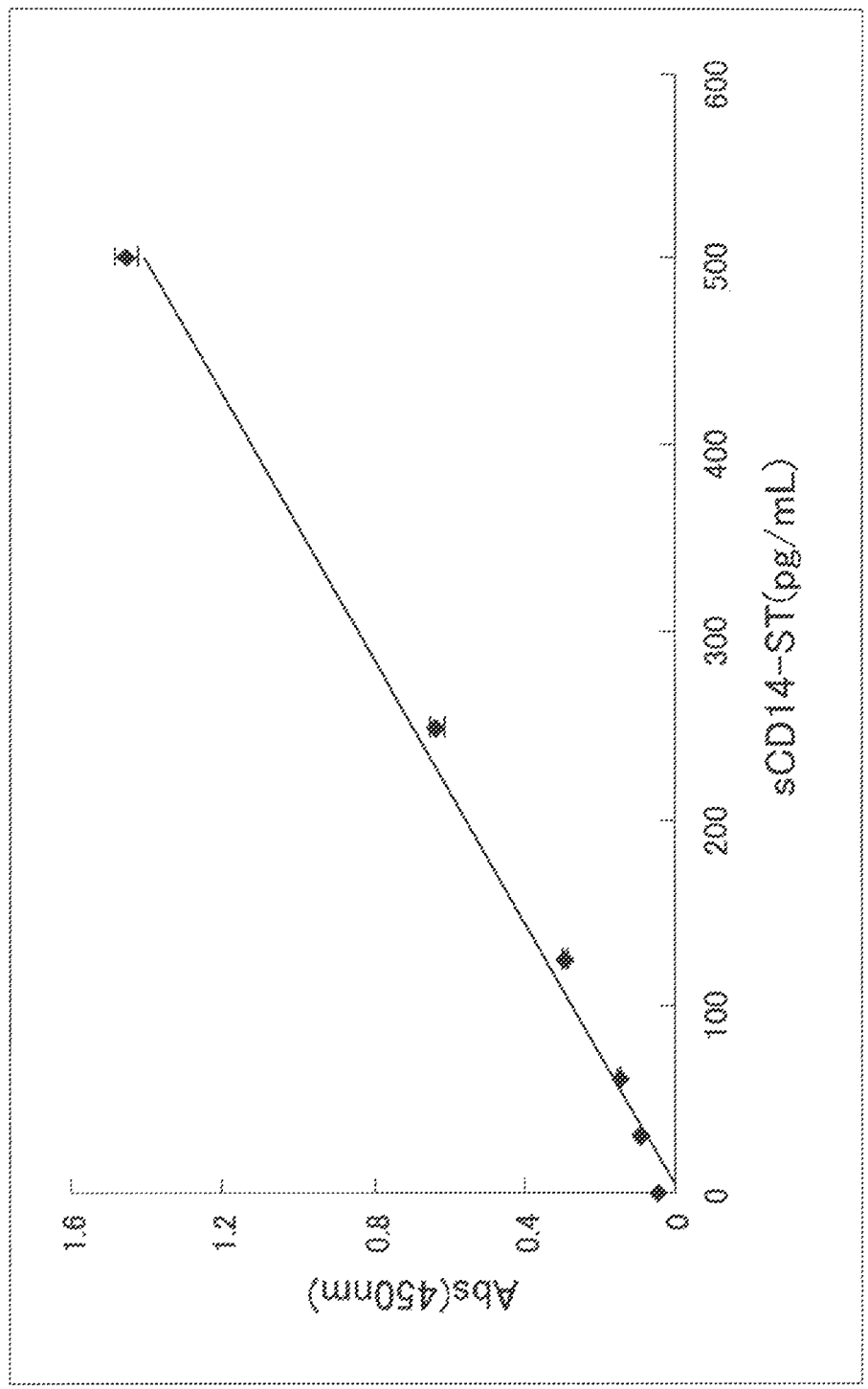
FIG. 1 shows dose dependent reactivity of recombinant rabbit sCD14-ST in the sCD14-ST assay system described in Example 3. The horizontal axis is concentration (pg/mL) of the recombinant sCD14-ST, and the longitudinal axis is absorbance.

DESCRIPTION OF EMBODIMENTS 1. sCD14-ST (Soluble CD14 Antigen Subtype)

The present invention is based on the finding that sCD14-ST is produced in the process of the engulfing and digestion of the foreign microorganism or foreign substance by the phagocyte. Of the sCD14, sCD14-ST has the characteristic that it is electrophoresed in SDS-PAGE to a molecular weight of 13±2 kDa under the non-reducing conditions, and it has retained the amino acid sequence of the CD14 on N terminal side. sCD14-ST also exhibits immunogenicity which is different from the high molecular weight sCD14. For example, while the human high molecular weight sCD14 is recognized by 3C10 antibody (ATCC TIB-228), human sCD14-ST does not bond to the 3C10 antibody.

In the meanwhile, some antibodies specifically recognize the sCD14-ST while failing to recognize the high molecular weight sCD14. Such antibody is the peptide antibody whose epitope is the peptide at particular domain of the sCD14-ST, and the particular domain is the region between β3 and β4 in the secondary structure of the CD14 (Kim et al., Journal of Biological Chemistry, 280: 11347-11351, 2005). More specifically, the particular domain corresponds to 36th to 79th amino acid sequence in human CD14 (SEQ ID NO. 1), 38th to 81st amino acid sequence in rabbit CD14 (SEQ ID NO. 2), 36th to 79th amino acid sequence in mouse CD14 (SEQ ID NO. 3), and 36th to 77th amino acid sequence in bovine CD14 (SEQ ID NO. 4). The antibody is produced by using a peptide consisting consecutive 8 or more amino acids in the region for the antigen. The preferred are the peptide comprising 16 amino acids from 53rd to 68th of human CD14, and the peptide consisting 20 amino acids from 40th to 59th of rabbit CD14. While the region of β3 to β4 (including β3-α2-α3-β4) of the high molecular weight sCD14 has β sheet structure or α helix structure, the region of β3 to β4 in the sCD14-ST can not retain its inherent tertiary structure since its sequence lacks substantial portion on its C terminal side compared to the high molecular weight sCD14. Such difference in the tertiary structure is believed to result in the difference of the recognizability by the antibody.

Accordingly, the sCD14-ST can be characterized by the unique immunogenicity in addition to its electrophoresis to the molecular weight of 13±2 kDa under non-reducing conditions in SDS-PAGE and its retention of the N terminal region of the CD14. The "unique immunogenicity" means that it is recognized by the antibody produced by using an antigen comprising consecutive 8 or more amino acids in the β3 to β4 region of the CD14 for the antigen. sCD14-ST is also a factor which shows specific increase of the blood concentration in the case of sepsis or in the sepsis model animal induced by infection by living bacteria. For example, human sCD14-ST is electrophoresed in the SDS-PAGE to a molecular weight of 13±2 kDa under non-reducing conditions, and has on it N terminal side the sequence comprising 1st to 8th amino acid residues of the amino acid sequence defined in SEQ ID NO. 1, and it specifically binds to an antibody binding to the peptide consisting 16 amino acid residue at 53rd to 68th of the amino acid sequence defined in SEQ ID NO. 1. Furthermore, it may additionally have at least one characteristic feature selected from its specific binding to an antibody which binds to the peptide consisting 17th to 26th amino acid residues of the amino acid sequence defined in SEQ ID NO. 1; not binding to 3C10 antibody; not binding to MEM-18 antibody; not having LPS-binding ability; being obtainable from human serum; and being a factor which exhibits specific blood concentration increase in the sepsis patients.

Since the sCD14-ST retains the amino acid sequence at the N terminal of the CD14, when the sCD14-ST is isolated and its N terminal amino acid sequence is analyzed, it includes the same amino acid sequence as the N terminal of the CD14. The requirement is that the amino acid sequence of at least 1st to 8th at the N terminal amino acid is the same as the CD14. For example, in the case of human, the sCD14-ST can be confirmed to have the sequence of 1st to 8th in the amino acid sequence of SEQ ID NO. 1, and in the case of rabbit, it would be confirmed to have the sequence of 1st to 8th in the amino acid sequence of SEQ ID NO. 2; in the case of mouse, it would be confirmed to have the sequence of 1st to 8th in the amino acid sequence of SEQ ID NO. 3; and in the case of bovine, it would be confirmed to have the sequence of 1st to 8th in the amino acid sequence of SEQ ID NO. 4.

2. Method for Evaluating the Function of a Phagocyte

The phagocyte used in the present invention is not particularly limited as long as it has phagocytosis activity and it is from a mammal. The preferred, however, is a neutrophil. In view of the ease of preparation, leukocyte or granulocyte may be used as the specimen containing the neutrophil. Isolated cell line having the function of differentiating into granulocyte may also be used, and exemplary such cell lines include HL-60. Exemplary mammals include human, rabbit, mouse, rat, monkey, bovine, pig, sheep, goat, horse, dog, and cat.

The phagocyte may be prepared from body fluids such as blood, interstitial fluid, lymph, synovial fluid, milk, cerebrospinal fluid, pus, saliva, lacrimal fluid, mucus, nasal discharge, sputum, urine, ascites, amniotic fluid, and seminal fluid. The phagocyte may also be prepared from lavage fluid of nasal cavity, bronchus, lung, skin, peritoneal cavity, various organs, joint, bone, and the like, or from a tissue such as skin, lung, kidney, and mucus.

When the phagocyte is prepared from a living body, only phagocyte may be strictly isolated, or alternatively, a fraction containing phagocyte may be prepared. For example, leukocyte from blood, granulocyte from blood, and granulocyte from peritoneal lavage fluid may be used for the phagocyte used in the method of the present invention.

The function of the phagocyte is the physiological function that is possessed by the phagocyte. In the present invention, the function of a phagocyte is evaluated by using the phagocytosis for the index of the phagocyte activity. The phagocyte may also have various functions such as the function of producing cytokines and the function of migration depending on the type of the phagocyte. However, the function common to all phagocytes is the phagocytosis. Accordingly, phagocytosis is preferably used for the index in determining whether the phagocyte has normal function as the phagocyte. In addition, since most types of phagocytes have immune function as an immune cell in the living body, evaluation of the phagocytosis of the phagocyte may mean evaluation of the immune function of the phagocyte.

Accordingly, one preferred embodiment of the present invention is a method for assaying phagocytosis ability of the neutrophil, granulocyte, and/or leukocyte. Another preferred embodiment of the present invention is a method for evaluating immune function by assaying phagocytosis ability of the neutrophil, granulocyte, and/or leukocyte.

The method for evaluating the function of a phagocyte of the present invention is characterized by its measurement of the sCD14-ST produced by the phagocyte. sCD14-ST is useful as a marker for evaluating the function of a phagocyte since it is produced during the phagocytosis by the phagocyte. The phagocytosis by the phagocyte starts upon contact of the phagocyte with a substance to be engulfed. The substance to be engulfed is a substance which induces the phagocytosis of the phagocyte, and the term "phagocytosis" used herein means the process which at least includes engulfing of the substance to be engulfed by the phagocyte and digestion in the cell of the engulfed substance. Examples of the "substance to be engulfed" which is engulfed and digested by the phagocyte include cells such as bacteria and fungi as well as zymosan. In the meanwhile, a substance such as microbeads or latex beads which will not be digested after the engulfing is not the substance to be engulfed of the present invention.

The measurement of the sCD14-ST is conducted by using a solution containing a phagocyte or its supernatant. The term "solution" used herein means a culture medium, a cell fractionation solution, a cell assay solution, a physiological saline solution, a body fluid, and the like. When the phagocyte is prepared from a living body, and the phagocyte is already in the process of engulfing the endogenous substance to be engulfed, the function of the phagocyte can be evaluated by directly assaying the thus prepared phagocyte-containing solution or its supernatant.

When the substance to be engulfed is brought in contact with the phagocyte, the substance to be engulfed may be added to the solution containing the phagocyte. Alternatively, the solution containing the phagocyte may be added to a container having the substance to be engulfed immobilized to its interior surface. The substance to be engulfed is preferably zymosan in view of the ease of handling.

The system used for the measurement of the sCD14-ST is not particularly limited as long as the sCD14-ST is detected. The preferred, however, is the immunological assay using an antibody which specifically binds to the sCD14-ST. The immunological assay system is preferably selected from direct adsorption, sandwich method, aggregation, solid phase immobilization, and reaction in a solution. The most preferred is the use of sandwich method (sandwich immunoassay).

Sandwich immunoassay is a method in which at least two types of antibodies each recognizing different site of the protein to be assayed are used to form an antibody-antigen-antibody complex. The sandwich immunoassay can be carried out by the methods known in the art, and the assay principle, applications, and improvements are described, for example, in Eiji Ishikawa "Ultrahigh sensitivity enzyme immunoassay method", Gakkai Shuppan Center (1993); Nao Matsuhashi et al. ed. "New uses of immunoassay and use of immunoassay for the development of diagnostic and therapeutic drugs", Keiei-Kyouiku Shuppan (1985); and Eiji Ishikawa et al. ed. "Enzyme immunoassay" (3rd ed.), Igaku-Shoin (1987).

The antibody which specifically binds to the sCD14-ST is an antibody which binds to a peptide comprising the sequence of 8 or more consecutive amino acid residues in the region between β3 and β4 in the secondary structure of CD14. Examples of such antibodies include S68 antibody described in WO 2005/108429 and F1301-9-1 antibody described in Example 1 of the present invention. Use of another antibody is required when sandwich immunoassay is used, and this antibody does not have to be an antibody which specifically binds to the sCD14-ST, and such antibody may also be an antibody which recognizes both the high molecular weight sCD14 and the sCD14-ST. Examples of such antibodies include F1106-13-3 antibody and F1031-8-3 antibody described in WO 2005/108429 and F1258-7-2 antibody described in Example 2 of the present invention. These antibodies may be either a polyclonal antibody or a monoclonal antibody. In the case of the sandwich immunoassay, the antibodies used are preferably a monoclonal antibody. The antibody may also be a fragment of such monoclonal antibody. The term "antibody fragment" used herein means any one of the Fab, Fab', and F(ab')2 of such monoclonal antibody.

In the immunological assay system, existence the sCD14-ST is confirmed by forming a complex of the sCD14-ST with an antibody, and detecting the complex by means of the label attached to the complex. Exemplary labels include an enzyme such as peroxidase, alkaline phosphatase, β-D-galactosidase, oxidase, or uricase; a chemiluminescent substance such as acrydinium or its derivative, or aequorin or its analog; a fluorescent substance such as FITC or a lanthanoid such as europium (Eu) or samarium (Sm); and a colorant, gold colloid, colored latex, or an isotope. When a chemiluminescent substance, a fluorescent substance, or a colorant label, or an isotope is used for the label, the assay may be completed by optically detecting the label by an assay apparatus adequately selected for the label. When the assay is conducted by a kit based on immunochromatography or flow through method using a colorant, gold colloid, or colored latex for the label, the assay may be completed by visual inspection.

The immunological assay system may be provided in the form of a kit. In such a case, the kit should include an antibody which specifically binds to the sCD14-ST as a critical component, and also components required for enabling the detection of the complex by means of the label after forming the complex of the sCD14-ST and the antibody. For example, the kit may include an insoluble carrier (plastic plate, latex particles, etc.) having the antibody immobilized thereon, a marker enzyme such as peroxidase, a marker substance such as gold colloid, a chromogenic substrate such as tetramethyl benzidine (TMB), a specific binding substance for improving detection sensitivity such as biotin-streptavidin, a blocking agent, a dilute solution, a washing solution, a reference substance, and the like.

The sCD14-ST in the solution containing a phagocyte or its supernatant is qualitatively and/or quantitatively measured. The result of the measurement is compared with the standard value to determine the presence and/or amount of the sCD14-ST to thereby evaluate presence and/or degree of the phagocytosis by the phagocyte. The standard value may be adequately set depending on the object of the assay. For example, the result of the measurement for the solution not containing the phagocyte, the solution before contacting with the substance to be engulfed, or their supernatant may be used as the negative standard value. The phagocytosis by the phagocyte is evaluated by determining whether the measurement of the specimen is higher than the negative standard value. A calibration curve may also be depicted from the measurements of the sCD14-ST standard substance for use as the standard. In this case, the phagocytosis by the phagocyte is evaluated by comparing the measurement for the specimen with the calibration curve to determine the amount of the sCD14-ST in the specimen. The degree of the function of the phagocyte in the specimen or the degree of the activation of the phagocyte may be evaluated by using the standard value of the number of the phagocyte used in the assay and/or the amount of the sCD14-ST produced per unit time. The standard substance of the sCD14-ST may be the sCD14-ST purified from blood, sCD14-ST which has been produced by phagocytotic stimulus by the phagocyte followed by purification, recombinant sCD14-ST, or sCD14-ST produced by peptide synthesis. The method used for the purification of the sCD14-ST and the production method of the recombinant sCD14-ST are described in WO 2005/108429.

3. Various Detection and Evaluation Methods by Evaluating Function of the Phagocyte Collected from the Subject The following detection and evaluation is enabled if the function of the phagocyte collected from the subject is evaluated by using the method described in the section of "2. Method for evaluating the function of a phagocyte".

A) Detection and evaluation of whether the subject is suffering from a disease associated with dysfunction of the phagocyte, the stage of the disease, and/or severity of the disease.

B) Detection and evaluation of change such as decrease or enhancement, abnormality, and/or degree of the immune function of the subject.

C) Detection and evaluation of effect of the drug by evaluating the function of the phagocyte collected from the subject during and/or after the drug administration.

D) Provision of an index for the quality rating of the phagocyte when the phagocyte is used in regenerative medicine.

In detecting and evaluating the disease associated with phagocyte dysfunction, the process should at least include the step of evaluating the function of the phagocyte from the subject by using the method described in the section of "2. Method for evaluating the function of a phagocyte", and the process may further comprise the steps of comparing the evaluation results with the normal value, and determining the suffering and/or the degree of the disease based on whether the function of the phagocyte collected from the subject is higher or lower than the normal value.

The term "normal value" used herein means the value obtained by preliminarily measuring the function of the phagocyte collected from the subjects not suffering from the disease, namely, the healthy subjects, and standardizing the measurements by calculating the average of the measurements or selecting a certain range from the measurements. While comparison of the measurement of the specimen with the normal value may be conducted by simply comparing the values, (average±2SD) or (average±3SD) in the normal subjects may be used as cut off values, and the specimen with the measurement higher or lower than the cut off values may be determined to have phagocyte dysfunction. The measurement value may also be used for evaluating the stage of the disease and/or severity of the disease.

Examples of the disease associated with the phagocyte dysfunction include uremia, decrease in the activity of serum opsonin, complement deficiency, congenital phagocytosis dysfunction, chronic granulomatous disease, myeloperoxidase defect, leukemia, malignant lymphoma, bacterial endocarditis, diabetes, and hepatic cirrhosis. For example, chronic granulomatous disease is a congenital phagocyte dysfunction caused by the defect in the active oxygen production by the neutrophil which results in repeated suffering from serious infection by bacteria and fungi. The neutrophil from the patient suffering from the chronic granulomatous disease has the function of phagocytosis (engulfing of the foreign substance) but not the digestive function. Accordingly, abnormality can not be detected by the evaluation of the engulfing of the latex beads while evaluation of the phagocytosis using the production of the sCD14-ST for the index can detect the phagocyte dysfunction.

Evaluation of the immune function may be conducted according to the detection and evaluation of the disease associated with the phagocyte dysfunction. The function of a phagocyte, and in particular, the phagocytosis is an important defense mechanism at the earliest stage of the immune response, and phagocyte dysfunction leads to abnormal immune function. Accordingly, the evaluation of the immune function may be conducted by understanding the phagocyte dysfunction as the immune function.

In detecting and evaluating the effects of the drug, the process should at least include the step of evaluating the function of the phagocyte for the phagocyte collected from the subject during and/or after the drug administration by using the method described in the section of "2. Method for evaluating the function of a phagocyte", and the process may further comprise the steps of comparing the evaluation results with the normal value and/or the results before the drug administration, and determining the presence and/or the degree of the change in the function of the phagocyte collected from the subject by the drug administration. As described above, the term "normal value" is the measurement obtained by assaying the function of the phagocyte from healthy subjects.

If change in the function of a phagocyte during and/or after the drug administration could be detected after administering an immunosuppressant, an immunostimulant, an anticancer agent, or the like, effectiveness of the drug and the degree of the side effects can be confirmed, and this will serve a useful guideline for drug selection and determination of its dose. Degree of the change of the function of a phagocyte, namely, change in the amount of the sCD14-ST produced can be used for the index of the degree of the drug effectiveness. For example, phagocytosis of the neutrophil in the peripheral blood may be compared before and after the G-CSF administration to evaluate how the neutrophil having normal function had increased by the G-CSF administration.

When the phagocyte is evaluated for use of the phagocyte in regenerative medicine, the phagocyte used may be measured for its phagocytosis by using the production of the sCD14-ST for the index to thereby determine whether the phagocyte has the normal function as a phagocyte and/or the phagocyte activity. The term "regenerative medicine" used herein includes autologous cell transplantation in which leukocyte or the like collected from the patient is cultivated and treated outside the body of the patient and transplanted back into the patient as well as cross-cell transplantation in which the leukocyte or the like collected from a normal donor is transplanted to a patient. After the preparation of the phagocyte for transplantation, the method described in the section of "2. Method for evaluating the function of a phagocyte" may be used for testing whether the phagocyte has a certain quality. The function of the prepared phagocyte is compared with the standard value, and if the measured value exceeds the standard value, the phagocyte is determined to have a quality sufficient in the regenerative medicine. While the standard value may be adequately set depending on the object of the regenerative medicine, the evaluation may be conducted generally by comparison with the phagocytosis of the normal phagocyte. When the value measured is lower than the standard value, the phagocyte should be determined to have a quality inadequate for the transplantation due to the loss of the function or cell activity of the phagocyte in the process of its preparation.

4. Screening for a Substance which Regulates the Phagocytic Function

Screening for a substance which regulates the phagocytic function may also be conducted by using the method described in the section of "2. Method for evaluating the function of a phagocyte". More specifically, the present invention provides a method for screening a substance which regulates the phagocytic function comprising the steps of:

1) contacting a phagocyte with an analyte, 2) measuring the sCD14-ST produced by the phagocyte, and 3) evaluating effects of the analyte on the phagocytosis by the phagocyte.

The step of 1) contacting a phagocyte with an analyte may be carried out so that the phagocyte and the analyte are contacted in the presence of the substance to be engulfed.

The "a substance which regulates the phagocytic function" is a substance which promotes or suppresses the phagocytosis of the phagocyte. For example, when a known a substance which regulates the phagocytic function such as Wortomanin or Cytochalasin D is used for the analyte, and this analyte is brought in contact with the phagocyte to measure the sCD14-ST produced by the phagocyte, amount of the sCD14-ST produced decreases with the addition of the analyte, and the phagocytosis-suppressing effect is thereby confirmed. Similarly, a substance whose phagocytic function-regulating activity is to be evaluated may be used for the analyte, and this analyte may be contacted with the phagocyte to measure the amount of the sCD14-ST produced, and this amount of the sCD14-ST may be used as an index for the effect of the sCD14-ST on the phagocytosis.

5. Method for Detecting Disease Associated with Phagocytosis

The present invention also provides a method for detecting a disease associated with phagocytosis by the phagocyte. In this method, the sCD14-ST in the specimen collected from the subject is measured, and the result is compared with the normal value to determine whether the amount of the sCD14-ST in the specimen is higher than the normal value to thereby detect whether the subject is suffering from a disease associated with phagocytosis by the phagocyte, stage of the disease, and/or severity of the disease.

The test subject is not particularly limited as long as it is a mammal. Exemplary subjects include mammals such as human, monkey, rat, mouse, rabbit, bovine, pig, sheep, goat, horse, dog, and cat.

The disease associated with phagocytosis by the phagocyte is a disease in which phagocytosis by the phagocyte occurs in the lesion, and in particular, a disease associated with local phagocytosis by autoimmune response or infection. Exemplary such diseases include local diseases such as autoimmune diseases, rheumatoid arthritis, mastitis, gout, glomerulonephritis, ulcerous colitis, Mediterranean fever, otitis media, rhinitis, pneumonia, tuberculosis, cystitis, amniotic fluid infection, and pyosemia. However, diseases associated with systemic infection and sepsis are not included the present invention.

Exemplary specimen include body fluids such as interstitial fluid, lymph, synovial fluid, milk, cerebrospinal fluid, pus, saliva, lacrimal fluid, mucus, nasal discharge, sputum, urine, ascites, amniotic fluid, and seminal fluid as well as lavage fluid obtained after washing nasal cavity, bronchus, lung, skin, peritoneal cavity, various organs, joint, bone, and the like. However, blood is not to be used in the present invention.

The measurement of the sCD14-ST may be conducted according to the method described in the section of "2. Method for evaluating the function of a phagocyte".

The normal value used may be the value obtained by preliminarily measuring the subjects not suffering from the disease, namely, the healthy subjects, and standardizing the measurements by calculating the average of the measurements or selecting a certain range from the measurements. When the value measured for the specimen collected from a healthy subject is substantially equivalent with the background of the assay system, a value standardized by calculating the average of the background value or selecting a range may be used as the normal value. The background value of the assay system is the value measured for the assay system having not the specimen but the buffer and the assay solution added thereto. While comparison of the measurement of the specimen with the normal value may be conducted by simply comparing the values, (average+2SD) or (average+3SD) of the normal subjects may be used as cut off values, and the specimen with the measurement higher than the cut off value may be determined as positive. The measurement value may also be used for the determination of the stage of the disease and/or severity of the disease, and more specifically, a higher measurement value may mean higher stage and higher severity of the disease.

The specimen may or may not contain the phagocyte. The sCD14-ST in the specimen can be directly measured to evaluate the phagocytosis in the living body, namely, to determine the suffering from and/or severity of the disease, partly because the sCD14-ST produced as the results of the phagocytosis by the phagocyte in the living body is present in the specimen. For example, in the case of arthritis model animal, the sCD14-ST in synovial fluid or joint lavage fluid can be measured to diagnose the disease associated with inflammation at the joint, and in particular, rheumatoid arthritis, osteoarthritis, periarthritis scapulohumeralis, and the like, partly because increase in the concentration of the sCD14-ST in the synovial fluid or joint lavage fluid is detectable.

On the other hand, presence and/or amount of the phagocyte in the body fluid or tissue lavage fluid may be detected to thereby determine the suffering from and/or severity of the disease. In this case, a substance to be engulfed may be added to the specimen to measure the sCD14-ST produced. For example, a substance to be engulfed may be added to milk, and the sCD14-ST produced may be measured for diagnosing mastitis. This is particularly useful for detecting bovine mastitis.

The present invention has been described by referring preferred embodiments which by no means limit the scope of the invention. Various changes and modification may occur to those skilled in the art, and such changes and modification can be made without deviating the scope of the present invention.

EXAMPLES

Example 1

Production of F1301-9-1 Antibody by Using a Synthetic Peptide for the Antigen 1-(1) Preparation of the Peptide Used for the Antigen A peptide having the sequence defined in SEQ ID NO. 5 (corresponding to the sequence of 40th to 59th amino acid residues of rabbit CD14 amino acid sequence) having cysteine inserted at its N terminal for ligation at its end with the carrier protein via SH group was synthesized using peptide synthesizer ABI433A (Applied Biosystems). The peptide was purified by the method commonly used in the art to obtain 2 to 3 mg of the peptide.

1-(2) Preparation of Peptide Carrier Protein Using the Synthetic Peptide

The peptide prepared in 1-(1) was dissolved in distilled water to 10 mg/mL, and equal amount of this solution and 10 mg/mL Imject Maleimide Activated Keyhole Limpet Hemocyanin (KLH) (PIERCE) were mixed. The mixture was allowed to react at room temperature for 2 hours for the binding of the peptide with the carrier protein (this product is hereinafter referred to as "SEQ ID NO. 5 peptide—KLH"). In the meanwhile, the peptide prepared in 1-(1) was dissolved in distilled water to 10 mg/mL, equal amount of this solution and 10 mg/mL Imject Maleimide Activated Bovine Serum Albumin (BSA) (PIERCE) were mixed. The mixture was allowed to react at room temperature for 2 hours for the binding of the peptide with the carrier protein (this product is hereinafter referred to as "SEQ ID NO. 5 peptide—BSA").

1-(3) Production of Hybridoma Clone by Using the Synthetic Peptide for the Antigen In order to prepare a monoclonal antibody for the peptide prepared in 1(1), rat was immunized with SEQ ID NO. 5 peptide—KLH. More specifically, 100 μg of SEQ ID NO. 5 peptide—KLH was diluted with 100 μL physiological saline, and equal amount of this solution and 100 μL Freund's complete adjuvant (DIFCO) were mixed. 100 μL of this mixture was administered to foot pad of a female 8 week-old Wistar rat (Japan SLC, Inc.). After 11 days, 100 μg of SEQ ID NO. 5 peptide—KLH which had been diluted with 200 μL physiological saline was again administered to the foot pad. 3 days after the administration, lymphocytes were separated from ilium lymph node, and the thus obtained lymphocytes were mixed with Sp2/O—Ag14 (ATCC CRL-1581), and cell fusion was conducted according to the procedure described in "Introduction to experimental methods of monoclonal antibody" edited by Tamie Ando and Takeshi Chiba (Kodan-sha) by using polyethylene glycol. Hybridoma was selected by HAT medium, and after 1 week, the hybridoma producing the desired antibody was selected by ELISA. More specifically, SEQ ID NO. 5 peptide—BSA was diluted with 0.076M phosphate buffer (pH 7.4) (hereinafter referred to as D-PBS) to 10 μg/mL, and added to an immunoplate (Maxisorb, Nunc) at 50 μL/well. After allowing the reaction to proceed overnight at 4° C., the well was washed 5 times with ion exchanged water. The well was blocked by adding 100 μL of D-PBS (pH 7.4) containing 2% Stabilgurd to each well. Next, the supernatant of the hybridoma culture was added to each well, and after reacting at 37° C. for 1 hour, the well was washed 3 times by physiological saline containing 0.05% Tween 20. Peroxidase-labeled anti-rat immunoglobulin antibody (DAKO) was diluted 1000 times with D-PBS (pH 7.4) containing 10% rabbit serum, and 50 μL was added to each well. After reacting at 37° C. for 1 hour, the well was washed 3 times by the same procedure. TMB solution (BioFX) was added to each well, and after reacting at room temperature for 10 minutes, the reaction was ceased by adding 0.5M sulfuric acid solution. Absorbance at 450 nm was measured by plate spectrophotometer (NJ-2100, Intermed Japan), and the cells in the well with the increased absorbance were collected and cloned by limiting dilution analysis. After 11 days, screening was conducted by the same method, and clone F1301-9-1 producing the antibody which reacts with the peptide of SEQ ID NO. 5 was obtained.

1-(4) Purification of Antibody from the Supernatant of the Hybridoma

The F1301-9-1 obtained in 1-(3) was cultivated at 3 L scale in SFM medium (GIBCO). The supernatant of this medium was filtered through 0.45 μm filter to remove the cells, and the filtrate was applied to a Protein G column. Next, the adsorbed fraction was eluted with an acid, and the eluate was immediately neutralized by adding 1/10 volume of 1M Tris-HCl (pH 8.0). The eluate was subjected to buffer exchange with physiological saline by using an ultrafilter membrane to obtain the purified antibody.

Example 2

Preparation of F1258-7-2 Antibody by Using the Synthetic Peptide for the Antigen 2-(1) Preparation of the Peptide Used for the Antigen A peptide having the sequence defined in SEQ ID NO. 6 (corresponding to the sequence of 1st to 30th amino acids of rabbit CD14 amino acid sequence) having cysteine inserted at its N terminal for ligation at its end with the carrier protein via SH group was synthesized using peptide synthesizer ABI433A (Applied Biosystems). The peptide was purified by the method commonly used in the art to obtain 2 to 3 mg of the peptide.

2-(2) Preparation of Peptide Carrier Protein Using the Synthetic Peptide

SEQ ID NO. 6 peptide—KLH and SEQ ID NO. 6 peptide—BSA were prepared by the method similar to that of to 1-(2).

2-(3) Production of Hybridoma Clone by Using the Synthetic Peptide for the Antigen Clone F1258-7-2 producing the monoclonal antibody for the SEQ ID NO. 6 peptide prepared in 2-(2) was produced by the method similar to that of to 1-(3).

2-(4) Purification of Antibody from the Supernatant of the Hybridoma

A monoclonal antibody was purified from the supernatant of the culture of the hybridoma clone of the SEQ ID NO. 6 peptide prepared in 2-(3) by the method similar to that of to 1-(4).

Example 3

Preparation of the Assay System for Rabbit sCD14-ST

In order to prepare a system capable of specifically detecting of the rabbit sCD14-ST, a sandwich ELISA system was prepared by using the antibodies prepared in Example 1-(4) and Example 2-(4).

3-(1) Preparation of F1258-7-2 Fab'-HRP

To prepare F(ab')2 of the F1258-7-2 antibody, the purified F1258-7-2 antibody prepared in Example 2-(4) was treated with pepsin. More specifically, the purified F1258-7-2 antibody was subjected to buffer exchange with 100 mM acetate buffer (pH 4.4) containing 2M urea, and pepsin (Boehringer) was added so that antibody: enzyme was 30:1 (weight ratio). After the addition, the reaction was promoted at 37° C. for 6 hours. At the completion of the reaction, 1M Tris-hydrochloric acid buffer (pH 8.0) was added to bring the pH back to approximately neutral. Next, F(ab')2 was purified. More specifically, the antibody treated with pepsin was applied to Prosep G (Millipore) to remove the Fc moiety and the pepsin, and the adsorbed fraction was eluted with an acid. The adsorbed fraction was further applied to Superdex 200 (Amersham) to remove the uncleaved antibody to thereby obtain the F(ab')2 of the F1258-7-2. The purified F(ab')2 was confirmed for its purity by SDS-PAGE, and protein was quantitated by using Protein Assay Dye Reagent (Bio-Rad) using bovine serum IgG for the standard. The thus obtained F1258-7-2 F(ab')2 antibody was partially reduced by Peroxidase Labeling Kit SH (Dojindo Laboratories), and cysteine residue at the hinge was labeled with peroxidase to produce F1258-7-2 Fab'-HRP.

3-(2) Preparation of Rabbit sCD14-ST Sandwich ELISA System

Two step sandwich ELISA system was constructed by using the F1301-9-1 antibody produced in Example 1-(4) for the solid phase antibody, and the F1258-7-2 Fab'-HRP antibody prepared in Example 3-(1) for the labeling antibody. More specifically, the F1301-9-1 antibody was diluted with D-PBS (pH 7.4) to 10 μg/mL, and added to the wells of immunoplate (Maxisorb, Nunc) at 50 μL/well. After allowing the reaction to proceed overnight at 4° C., the well was washed 5 times with ion exchanged water. D-PBS (pH 7.4) containing 5% StabilGuard (SurModics) and 0.1%

Tween 20 was added to the wells at 200 μL/well for blocking. Next, the specimen was diluted by using 150 mM phosphate buffer (pH 6.0) containing 5% normal rabbit serum (serum from which soluble CD14 antigen has been removed by using the rabbit CD14 affinity antibody column), 1% BSA, and 0.1% Tween 20 for dilution, and the diluted specimen was added to the well at 50 μL/well and allowed to react at 25° C. for 3 hours. After completion of the reaction, the well was washed 5 times with physiological saline containing 0.05% Tween 20. The F1258-7-2 Fab'-HRP was diluted with 75 mM phosphate buffer (pH 6.4) containing 4% rat serum and 0.05% Tween 20, and added to the well at 50 μL/well. After allowing to react at 25° C. for 2 hours, the well was washed 5 times in the similar manner. Tetramethylbenzidine solution (TMB, BioFX) was added to the well, and the reaction was allowed to proceed at room temperature for 15 minutes. The reaction was ceased with 0.5M sulfuric acid solution, and absorbance at 450 nm was measured by using a plate spectrophotometer (NJ-2100, Intermed Japan).

The standard substance used was recombinant rabbit sCD14-ST. The recombinant rabbit sCD14-ST was prepared according to the method described in WO 2005/108429. More specifically, a plasmid having thrombin cleavage site inserted after 66th amino acid residue of the amino acid sequence of the rabbit CD14 was produced, and this plasmid was transiently expressed in the supernatant of COS cell culture. After purifying the sCD14 in the culture supernatant, the sCD14 was cleaved with thrombin and subjected to gel filtration chromatography to purify the recombinant rabbit sCD14-ST.

The thus prepared sandwich ELISA could detect the recombinant sCD14-ST in a dose-dependent manner as shown in FIG. 1.

Example 4

Examination of the sCD14-ST Production in Rabbit Subject Model 4-(1) Production of LPS-Induced Rabbit Sepsis Model LPS-induced rabbit sepsis model was prepared by administering LPS (Salmoella Minnesota Re595, Sigma) to auricular vein of a New Zealand white rabbit (1.8 to 2.6 kg, Kitayama Labes Co., Ltd.) at a dose of 10 μg/kg. Blood was collected from the auricular artery before and 1.5 hours after the LPS administration. Citric acid was added to the blood.

4-(2) Production of Rabbit Live Bacteria-Infected Model (CLP Model)

Rabbit CLP (cecal ligation and puncture) model was prepared by surgery of a New Zealand white rabbit (1.8 to 2.6 kg, Kitayama Labes Co., Ltd.). More specifically, the animal which had been fasted overnight underwent general anesthesia by administering 0.35 mg/kg of Domitor (medetomidine hydrochloride, Meiji Seika Kaisha, Ltd.) and 5 mg/kg of Ketalar for Animal (ketamine, Sankyo) to its auricular vein. After dissecting abdomen and taking cecum out of the peritoneal cavity, the cecum was ligated at the downstream of the ileocecum and 2 incisions each having a width of about 2 cm were made with ophthalmic scissors. The cecum was squeezed with forceps to confirm that the cecum content came out of the incision, and then, the cecum was placed back in the peritoneal cavity, and the peritoneum and the skin were closed with surgical suture. After closing the abdomen, 50 mL/kg of physiological saline was subcutaneously administered, and 0.35 mg/kg of Antisedan (atipamezole hydrochloride, Meiji Seika Kaisha, Ltd.) was administered to auricular vein to complete the surgery. Blood was collected from the auricular artery before and 2 hours after the surgery for the CLP model production. Citric acid was added to the blood.

4-(3) Measurement of the Blood sCD14-ST in the Rabbit Sepsis Model

Figure 2:
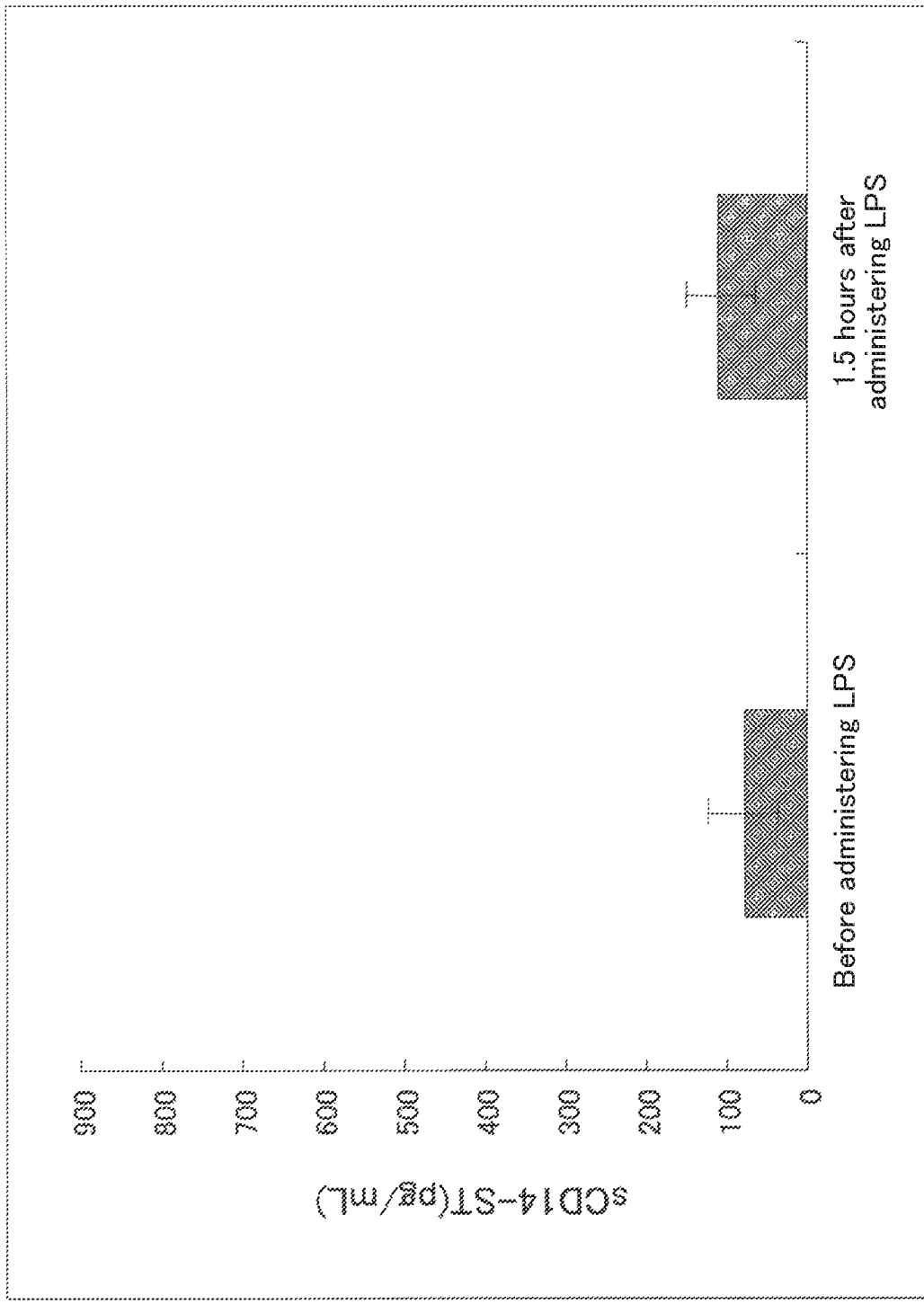
FIG. 2 shows measurements of the blood sCD14-ST before and after administering LPS to an LPS-induced rabbit sepsis model described in Example 4. The longitudinal axis is blood sCD14-ST concentration (pg/mL).
Figure 3:
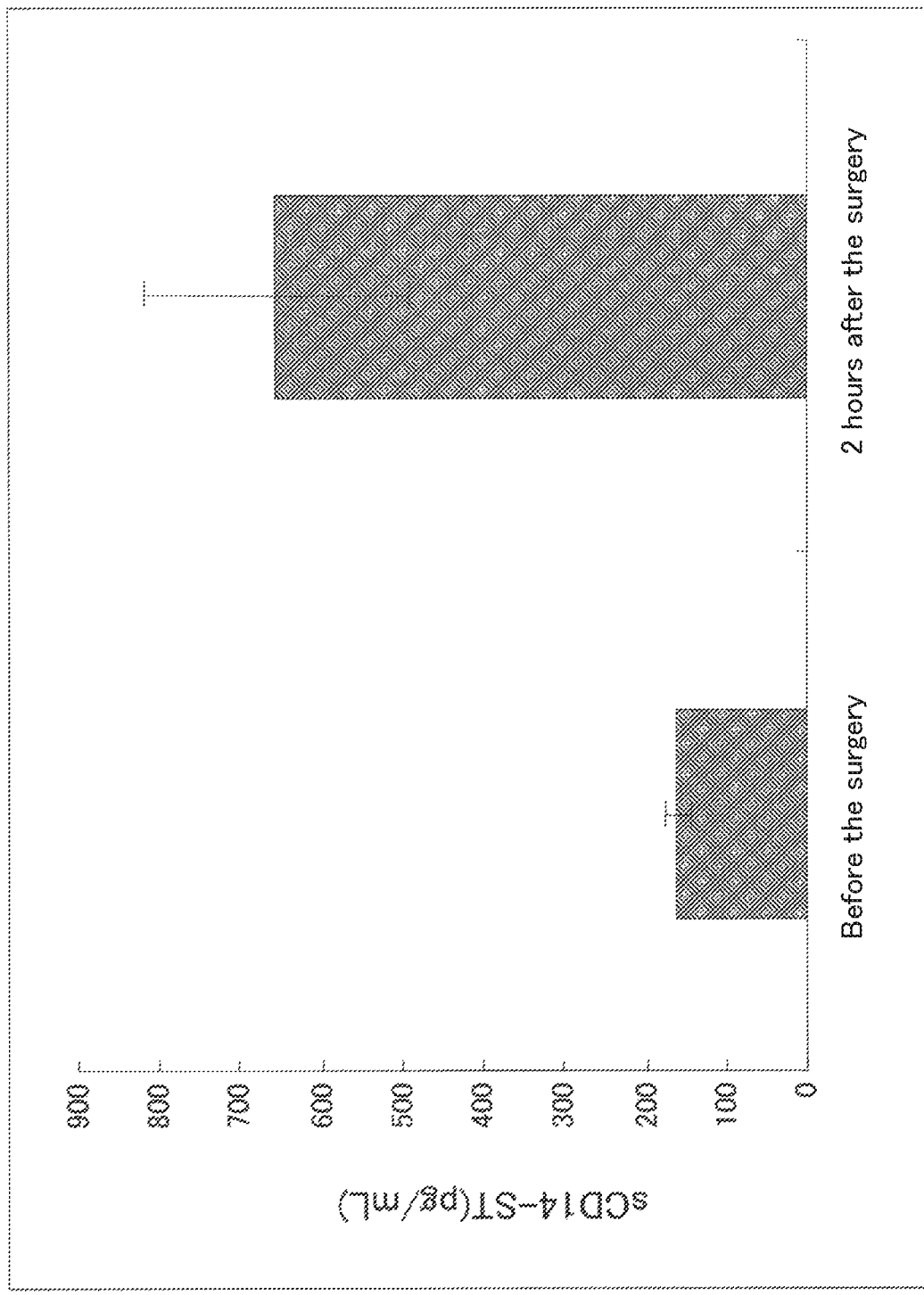
FIG. 3 shows measurements of the blood sCD14-ST before and after the surgery in the rabbit sepsis model prepared by live bacteria infection described in Example 4. The longitudinal axis is blood sCD14-ST concentration (pg/mL).

Plasma was prepared from the blood collected in Examples 4-(1) and 4-(2) by centrifugation, and sCD14-ST was measured according to the method described in Example 3-(2). The results are shown in FIGS. 2 and 3. Increase in the blood sCD14-ST was not recognized in the LPS-induced sepsis model (FIG. 2) while increase in the blood sCD14-ST was recognized in the case of the sepsis model by live bacteria infection (FIG. 3). The increase in the blood sCD14-ST in the sepsis model by live bacteria infection was detectable at 2 hours after the surgery (infection), confirming that the sCD14-ST is a marker which is detectable at an earlier stage of the infection compared to other markers such as IL-6 and d-dimer. These results indicated that the sCD14-ST production does not occur solely by the activation of the leukocyte by endotoxin, and necessity of the phagocytosis of the bacteria by leukocyte which is the immune reaction at the earliest stage of the infection.

Example 5

Phagocytosis Experiment Using Granulocyte from Rabbit Peritoneal Cavity 5-(1) Collection of Granulocyte from Rabbit Peritoneal Cavity Glycogen was dissolved with physiological saline to 0.1%, and 150 mL of this solution was administered to peritoneal cavity of New Zealand white male rabbit (Kitayama Labes Co., Ltd., 1.64 to 1.92 kg). 16 hours after the administration, the rabbit was euthanized by excessive anesthesia, and the peritoneal cavity was washed with physiological saline to collect the granulocyte.

5-(2) Production of sCD14-ST by Various Stimulants

Figure 4:
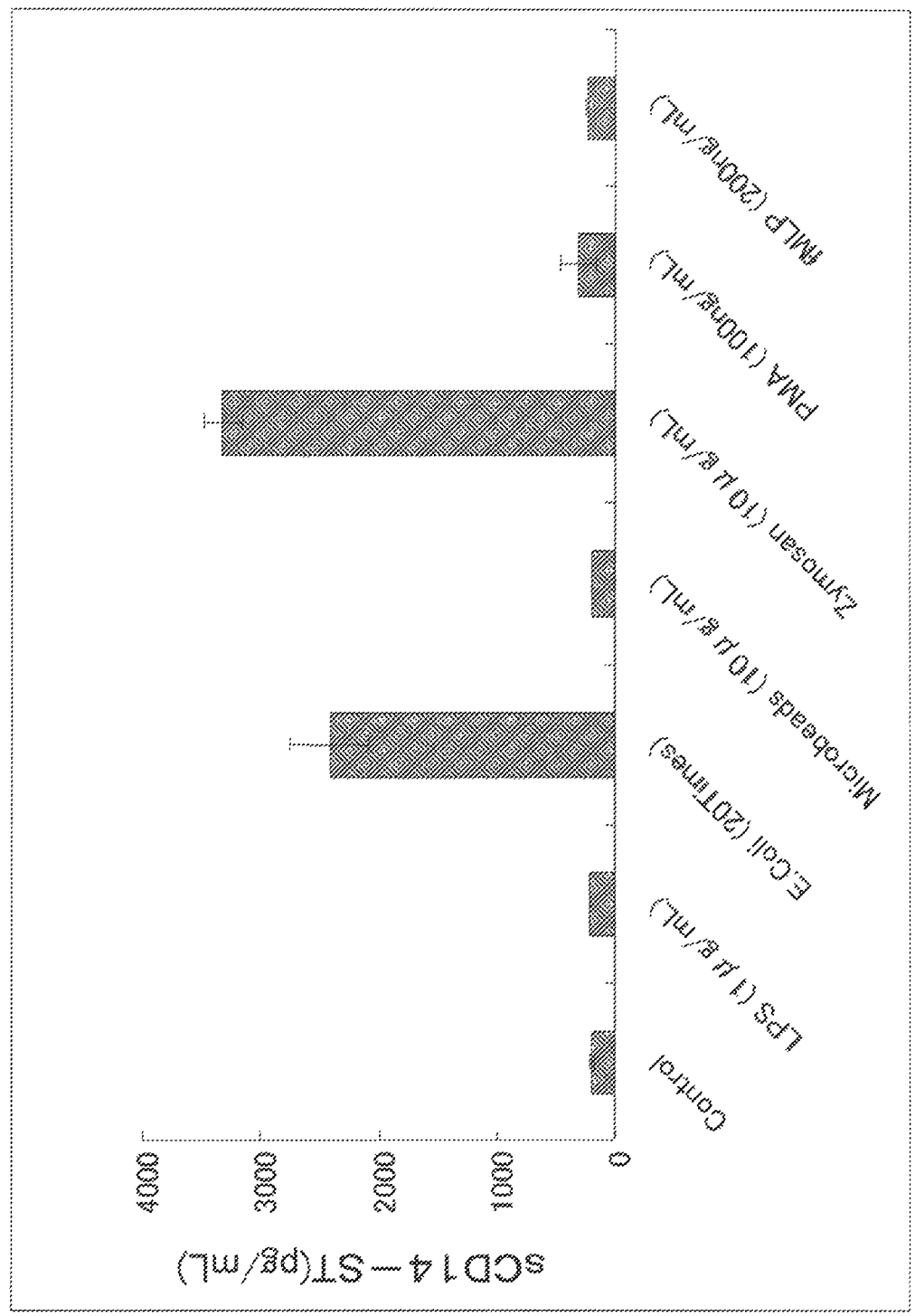
FIG. 4 shows production of the sCD14-ST when the rabbit granulocyte described in Example 5 is stimulated with various leukocyte stimulants.
Figure 5:
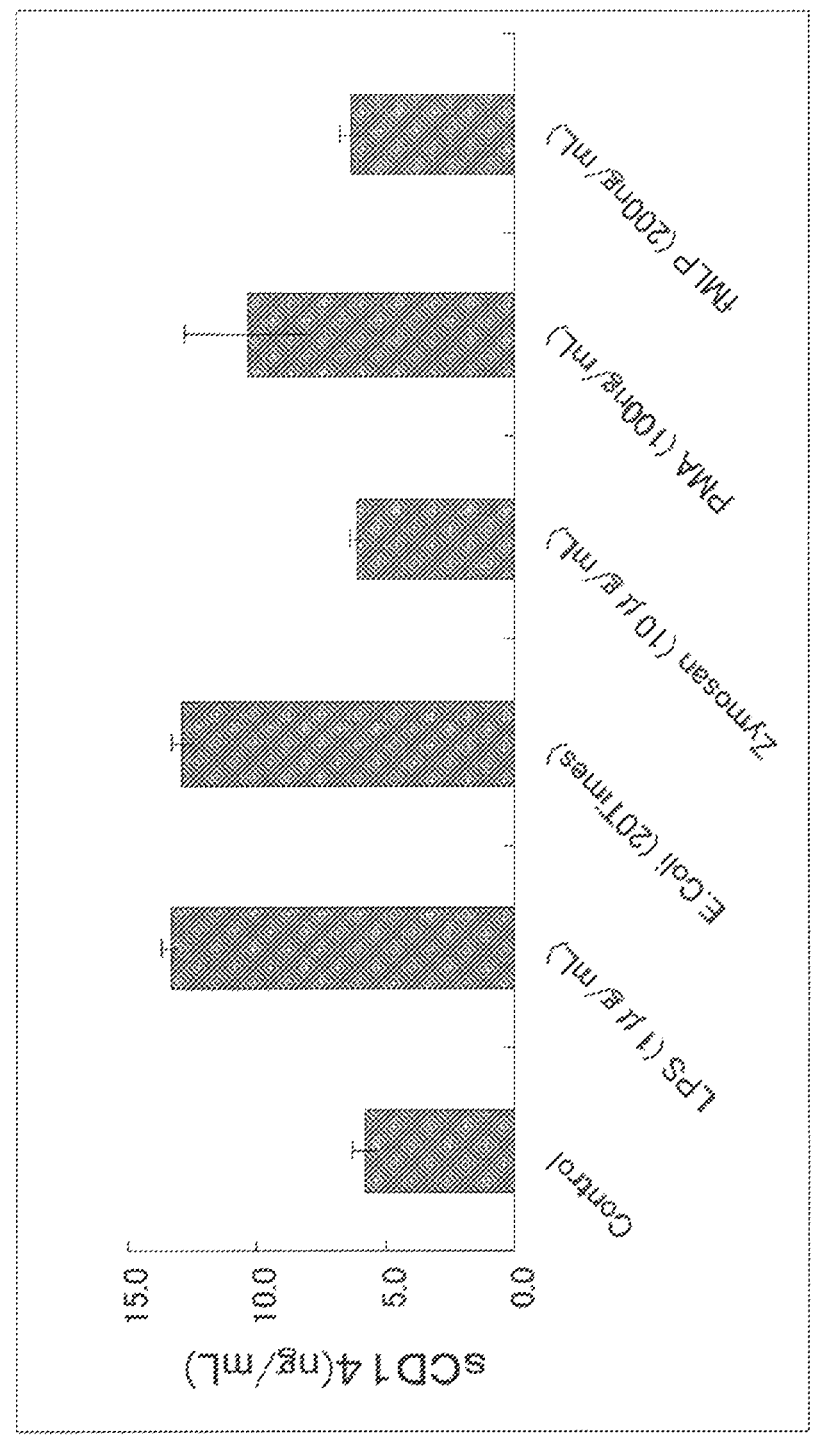
FIG. 5 shows production of the high molecular weight sCD14 when the rabbit granulocyte described in Example 5 is stimulated with various leukocyte stimulants.

Various leukocyte stimulants were added to the granulocyte to evaluate the amount of sCD14-ST produced. More specifically, granulocyte from the rabbit peritoneal cavity collected in Example 5-(1) was suspended in HBSS buffer (GIBCO 14025) containing 2% normal rabbit serum, 2 mM Glutamin, and 10 mM HEPES (hereinafter referred to as "cell assay buffer") to a cell concentration of $1 \times 10^7$ cells/mL, and added to the wells of 96 well culture plate (Nunclon Surface, Nunc) at 100 μL/well. Next, various stimulants were adjusted to 3 times the target concentration with the cell assay buffer, and added to the well at 50 μL/well. After incubating at 37° C. for 2 hours, the supernatant was collected by centrifugation and sCD14-ST was measured by the assay system of Example 3-(2). The results are shown in FIG. 4. Increase in the sCD14-ST was recognized in the case of the stimulants which induce phagocytosis and digestion by leukocyte (*E. coli* cell or zymosan). On the other hand, increase in the sCD14-ST was not recognized in the case of the stimulants not inducing the phagocytosis such as LPS, PMA (phorbol myristate acetate), and fMLP (formyl methionyl leucyl phenylalanine). Also, increase in the sCD14-ST was not recognized in the case microbeads which induce the phagocytosis but not the digestion. Next, production of high molecular weight sCD14 was measured by using a kit for measuring high molecular weight sCD14 (R&D), and increase in the production of the high molecular weight sCD14 was recognized after stimulating with the LPS or the PMA as shown in FIG. 5. These results indicate that the production mechanisms are different for the sCD14-ST and the high molecular weight sCD14.

5-(3) Action of Various Inhibitors on sCD14-ST Production

Figure 6:
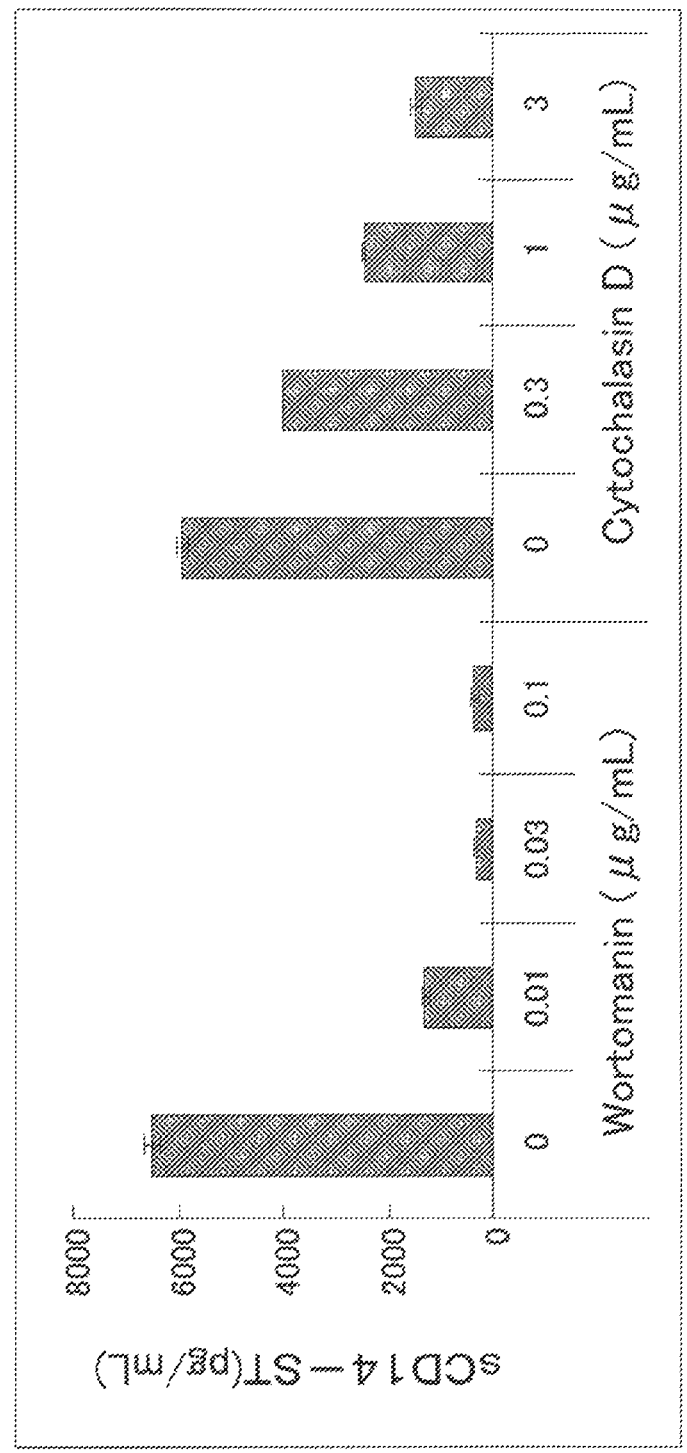
FIG. 6 shows effects of phagocytosis inhibitors on the sCD14-ST production when the rabbit granulocyte described in Example 5 is stimulated with the substance to be engulfed.

Example 5-(2) indicated that phagocytosis by the granulocyte is related to the production of the rabbit sCD14-ST. Accordingly, relation between the production of the sCD14-ST and the phagocytosis was examined by using various phagocytosis inhibitors. More specifically, the granulocyte from rabbit peritoneal cavity collected in Example 5-(1) was suspended in the cell assay buffer to a cell concentration of $1 \times 10^7$ cells/mL, and the suspension was added to the wells of 48 well culture plate (48 well Cell Culture Cluster, Corning) at 200 μL/well. Next, various inhibitors were adjusted to 3 times the target concentration with the cell assay buffer, and added to the well at 100 μL/well. After incubating at 37° C. for 30 minutes, 20 times by cell count of E. coli was added to the granulocyte (E. coli was added by counting 1 colony forming unit as 1 cell). After incubating at 37° C. for 2 hours, the supernatant was collected by centrifugation, and the sCD14-ST was assayed by using the assay system of Example 3-(2). The results are shown in FIG. 6. Production of the rabbit sCD14-ST was inhibited by PI3 kinase inhibitor Wortomanin which inhibits membrane traffic in the phagocytosis and by actin depolymerization agent Cytochalasin D which inhibits the phagocytosis by denaturing the cell skeleton.

Example 6

Measurement of sCD14-ST in Synovial Fluid in Rabbit Arthritis Model 6-(1) Preparation of Methylated BSA 1 g of BSA (SIGMA) was dissolved in 100 mL of D-PBS (pH 7.4) containing 4% paraformaldehyde, and after adjusting the pH to 8.5 by using an alkali, the reaction was allowed to proceed at room temperature for 1 hour. Next, 80 mg of sodium borohydride was added, and after allowing the reduction reaction to proceed at 4° C. for 2 hours, the buffer was exchanged with D-PBS (pH 7.4) by using a ultrafilter.

6-(2) Confirmation of Immune Reaction by ELISA

Immune reaction for the antigen was confirmed by ELISA. More specifically, methylated BSA was diluted with D-PBS (pH 7.4) to 10 μg/mL, and added to immunoplate (Maxisorp, Nunc) at 50 μL/well. After allowing the reaction to proceed at 37° C. for 1 hour and washing 5 times with ion exchanged water, the well was blocked by adding 100 μL/well of D-PBS (pH 7.4) containing 5% StabilGuard (SurModics). Next, the blood samples (serum) of the rabbits used in the evaluation of Example 6-(3) were diluted with D-PBS (pH 7.4) containing 1% StabilGuard (SurModics), and added to the well at 100 μL/well. After the reaction at room temperature for 1 hour, the well was washed 5 times with physiological saline containing 0.05% Tween 20. Next, peroxidase-labeled anti-rabbit immunoglobulin antibody (DAKO, P448) was diluted 1000 times with D-PBS containing 5% goat serum, and added to the well at 50 μL/well. After allowing to react at room temperature for 1 hour, the well was washed 5 times in the similar manner. TMB solution (BioFX) was added to the well, and the reaction was allowed to proceed at room temperature for 10 minutes. The reaction was ceased with 0.5M sulfuric acid solution, and absorbance at 450 nm was measured by using a plate spectrophotometer (Multiscan JX, Dainippon Pharmaceutical Co., Ltd.).

6-(3) Measurement of sCD14-ST in Rabbit Arthritis Model

Figure 7:
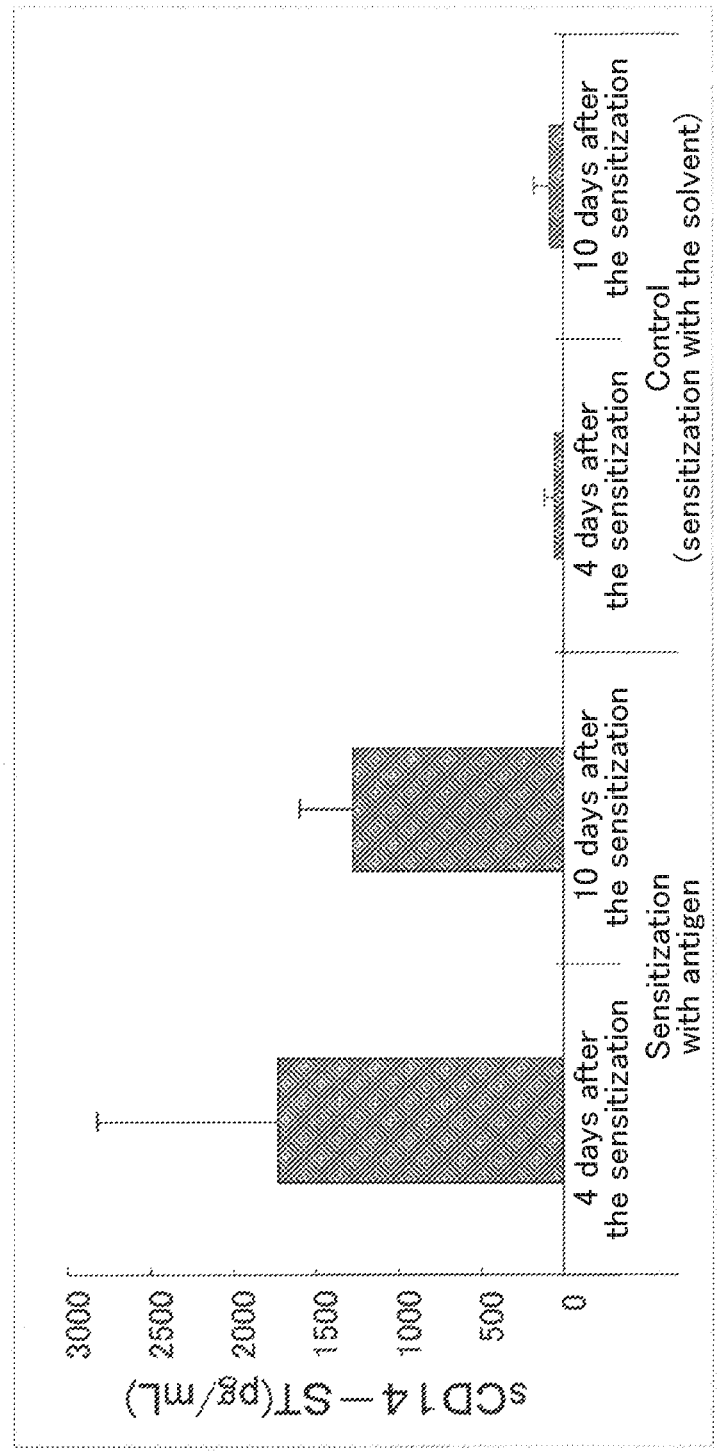
FIG. 7 shows measurements of sCD14-ST for the joint lavage fluid of the rabbit arthritis model described in Example 6.

500 μL (5 mg) of the methylated BSA prepared in Example 6-(1) and 500 μL of complete Freund's adjuvant (DIFCO) were mixed, and this mixture was administered subcutaneously at the back, at the sole of the hind leg, and intramuscularly at the thigh of New Zealand white male rabbits (10 to 11 week old, Kitayama Labes Co., Ltd.) (hereinafter referred to as the "antigen-sensitized group"). Simultaneously, the solvent having no methylated BSA added thereto was administered to the same number of rabbits (hereinafter referred to as the "solvent control group"). After 2 weeks, 500 μL (5 mg) of methylated BSA and 500 μL of incomplete Freund's adjuvant (DIFCO) were mixed, and this mixture was used to again sensitize the antigen-sensitized group. For the solvent control group, the solvent having no methylated BSA added thereto was added in similar manner. After 1 week, blood was collected from rabbit auricular artery, and antibody titer of the blood was measured by using the ELISA procedure described in Example 6-(2) to confirm that the sensitization had been established in the antigen-sensitized group. Next, the methylated BSA was adjusted by D-PBS (pH 7.4) to 5 mg/mL, and 1 mL was administered to the knee joint cavity of the antigen-sensitized group to induce arthritis. Simultaneously, 1 mL of D-PBS (pH 7.4) was administered to the knee joint cavity of the solvent control group. 4 days and 10 days after the induction, lavage fluid of the knee joint cavity was collected from both groups, and measurement of the sCD14-ST and analysis of blood cell fraction by smearing were conducted. Simultaneously, blood was collected from auricular artery (by adding citric acid to the blood) to measure blood sCD14-ST. In the smear sample, accumulation of a large number of granulocytes was recognized in the antigen-sensitized group. In addition, when the lavage fluid of the knee joint cavity was analyzed by the sCD14-ST assay system described in Example 3-(2), increase in the sCD14-ST was recognized in the antigen-sensitized group 4 days and 10 days after the antigen sensitization as shown in FIG. 7. The value was still high after 10 days, and this indicates that the sCD14-ST was produced by the phagocytosis caused by the excessive immune reaction against the self-tissue associated with arthritis. On the other hand, increase in the blood sCD14-ST was not recognized in both groups.

Example 7

Production of sCD14-ST Associated with the Phagocytosis of the Phagocyte from Human 7-(1) Preparation of Human Peripheral Blood Granulocyte Granulocyte fraction was prepared from peripheral blood collected from a healthy human donor by density-gradient centrifugation using two layers each having a specific gravity of d=1.077 and d=1.119.

7-(2) Production of sCD14-ST by the Phagocytosis of Granulocyte

Figure 8:
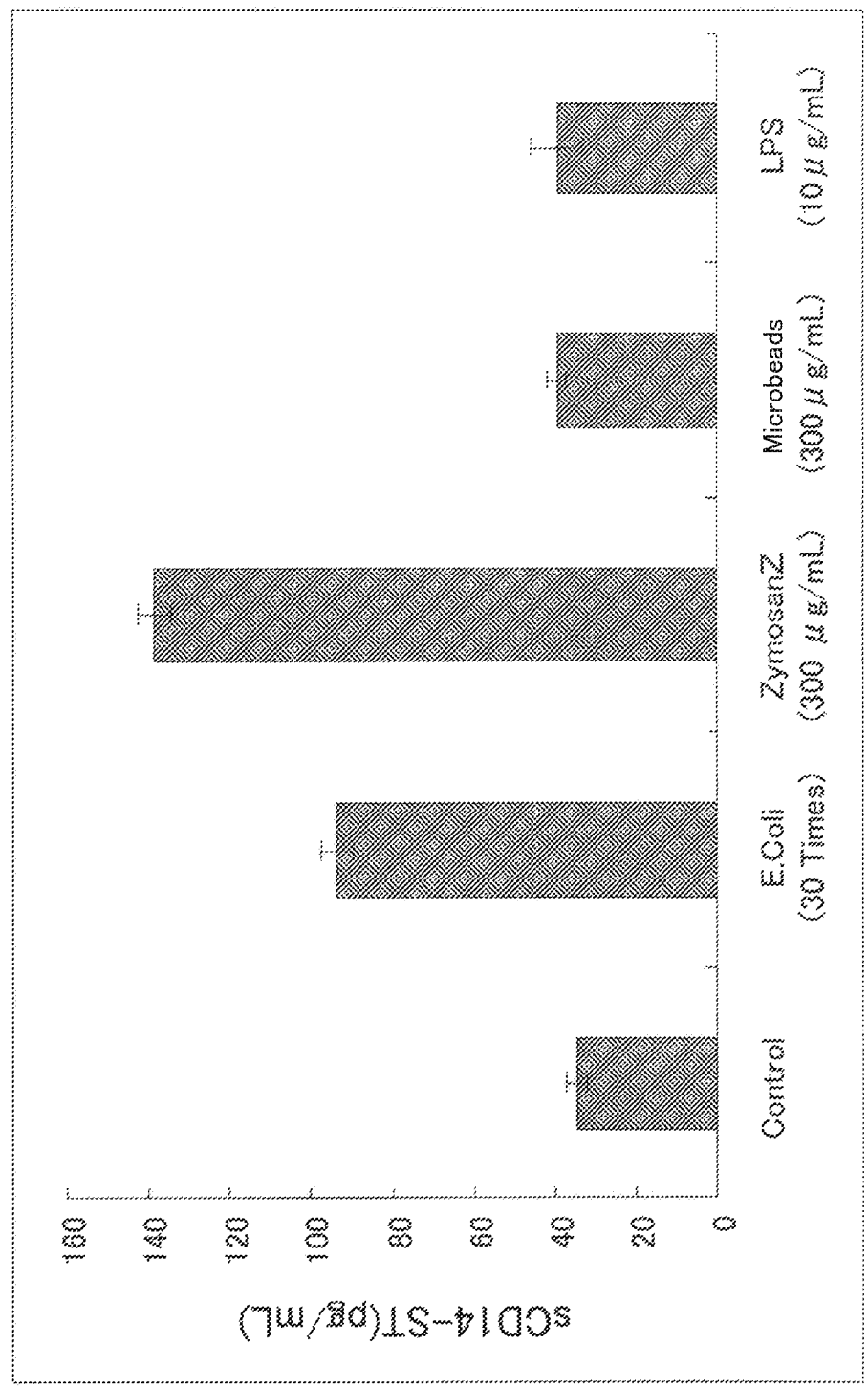
FIG. 8 shows production of the sCD14-ST when the human granulocyte described in Example 7 is stimulated by various leukocyte stimulants.

Various leukocyte stimulants were added to the granulocyte to evaluate the amount of sCD14-ST produced. More specifically, human peripheral blood granulocyte collected in Example 7-(1) was suspended in RPMI1640 culture containing 10% healthy human serum, 2 mM Glutamin, 10 mM HEPES, and 10 ng/ml G-CSF (SIGMA R8758) to a cell concentration of $0.5 \times 10^7$ cells/mL, and added to the wells of a 96 well culture plate (Nunclon Surface, Nunc) at 100 μL/well. The granulocyte was incubated overnight at 37° C.

in the presence of 5% carbon dioxide. Next, various stimulants were adjusted to 1.5 fold concentration with HBSS buffer containing 10% healthy human serum, 2 mM Glutamin, and 10 mM HEPES, and added to the well at 200 μL/well. After incubating at 37° C. for 2 hours, the supernatant was collected by centrifugation, and human sCD14-ST was measured by using the assay kit described in Example 7-(3) of WO 2005/108429. More specifically, the sandwich assay kit used was the one containing the antibody which binds to the peptide consisting the amino acid sequence of 53rd to 68th amino acid residue of the human CD14 (S68 antibody), which specifically recognizes the human sCD14-ST. To constitute the sandwich assay kit, another antibody which binds to the peptide consisting the amino acid sequence of 17th to 26th amino acid residue of the human CD14 (F1106-13-3), which has been labeled with peroxidase, was used. As shown in FIG. 8, and as in the case of Example 5, increase in the sCD14-ST was recognized with the phagocytosis stimulants (E. coli cell and zymosan) while increase in the sCD14-ST was not recognized with the LPS or the microbeads.

7-(3) Action of Phagocytosis Inhibitor for the Production of sCD14-ST

Figure 9:
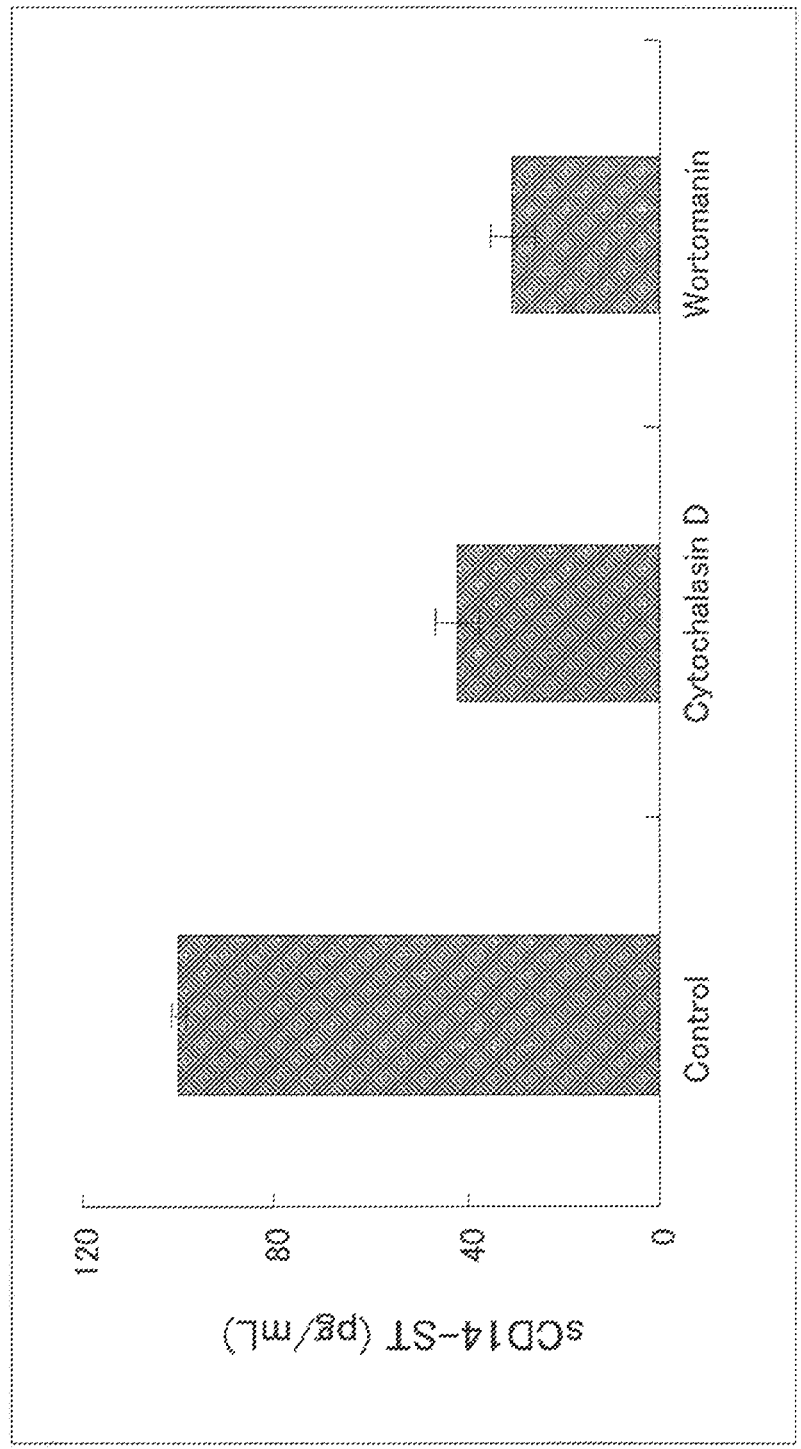
FIG. 9 shows effects of phagocytosis inhibitors on the sCD14-ST production when human granulocyte described in Example 7 is stimulated with the substance to be engulfed.

Action of the phagocytosis inhibitor on the sCD14-ST production by human granulocyte was examined. More specifically, human peripheral blood granulocyte was cultivated overnight on a 96 well culture plate as in the case of Example 7-(2). Next, various phagocytosis inhibitors was adjusted to 3 fold concentration with HBSS buffer containing 10% healthy human serum, 2 mM Glutamin, and 10 mM HEPES, and added to the well at 100 μL/well. After incubating at 37° C. for 1 hour, 30 times by cell count of E. coli was added to the granulocyte (E. coli was added by counting 1 colony forming unit as 1 cell). After incubating at 37° C. for 2 hours, the supernatant was collected by centrifugation, and the human sCD14-ST was assayed by using the assay kit described in Example 7-(3) of WO 2005/108429. The results are shown in FIG. 9. As in the case of Example 5-(3), Wortomanin and Cytochalasin D inhibited the sCD14-ST production.

7-(4) Experiment of the Phagocytosis by Using HL-60 Cell

HL-60 cell was cultivated in the presence of DMSO for differentiation into granulocyte, and then used for the experiment similar to Example 7-(2). Production of the sCD14-ST by the addition of zymosan or E. coli was recognized as in the case of the Example 7-(2).

The Examples as described above are some of the preferred embodiments of the present invention, and the present invention is not limited by these Examples. Various changes and modification may be made to these embodiments without deviating from the scope of the present invention.

SEQUENCE LISTING

The invention claimed is:

1. A method for detecting a disease associated with phagocytosis by a phagocyte comprising the steps of:

obtaining a specimen from a subject, wherein said specimen is at least one body fluid selected from the group consisting of interstitial fluid, lymph, synovial fluid, milk, cerebrospinal fluid, pus, saliva, lacrimal fluid, mucus, nasal discharge, sputum, urine, ascites, amniotic fluid, seminal fluid and lavage fluids obtained after washing naval cavity, bronchus, lung, skin, peritoneal cavity and various organs;

adding to the specimen a substance which increases phagocytic activity and which is engulfed by phagocytes in the specimen and which induces phagocytes in the specimen to produce an amount of sCD14-ST before measuring a total amount of sCD14-ST in the specimen;

measuring the total amount of sCD14-ST, including the amount sCD14-ST which is produced by phagocytes after the phagocytosis of the substance;

comparing the measured value with a standard value;

determining whether the amount of the sCD14-ST in the specimen is higher than the standard value; and detecting a disease associated with phagocytosis by a phagocyte in the subject when the measured value is higher than the standard value, wherein the sCD14-ST is measured by a sandwich immunoassay system comprising:

(a) an antibody binding to a peptide comprising 16 amino acids spanning from $53^{rd}$ to $68^{th}$ amino acids of human CD14 of SEQ ID NO: 1, and (b) an antibody binding to a peptide comprising an amino acid sequence at position 17 to 26 of SEQ ID NO: 1.

2. A method for detecting a rheumatoid arthritis, which comprises the steps of
obtaining a specimen from a subject, wherein said specimen is a synovial fluid:
adding to the specimen a substance which increases phagocytic activity and which is engulfed by phagocytes in the specimen before measuring the amount of sCD14-ST in the specimen;
measuring the amount of sCD14-ST which is produced by phagocytes after the phagocytosis of the substance;
comparing the measured value with a standard value;
determining whether the amount of the sCD14-ST in the specimen is higher than the standard value; and
detecting rheumatoid arthritis in the subject when a measured value is higher than the standard value, and
wherein the sCD14-ST is measured by a sandwich immunoassay system comprising:
(a) an antibody binding to a peptide comprising 16 amino acids spanning from 53rd to 68th amino acids of human CD14 of SEQ ID NO:1, and
(b) an antibody binding to a peptide comprising an amino acid sequence at position 17 to 26 of SEQ ID NO: 1.

3. A method for detecting mastitis, which comprises the steps of:
obtaining a specimen from a subject, wherein said specimen comprises milk:
adding to the specimen a substance which increases phagocytic activity and which is engulfed by phagocytes in the specimen before measuring the amount of sCD14-ST in the specimen;
measuring the amount of sCD14-ST which is produced by phagocytes after the phagocytosis of the substance;
comparing the measured value with a standard value;
determining whether the amount of the sCD14-ST in the specimen is higher than the standard value; and
detecting mastitis in the subject when a measured value is higher than the standard value, and
wherein the sCD14-ST is measured by a sandwich immunoassay system comprising:
(a) an antibody binding to a peptide comprising 16 amino acids spanning from 53rd to 68th amino acids of human CD14 of SEQ ID NO:1, and
(b) an antibody binding to a peptide comprising an amino acid sequence at position 17 to 26 of SEQ ID NO: 1.

4. The method according to claim 1, wherein said substance is zymosan.

* * * * *